(12) United States Patent
Goto

(10) Patent No.: US 9,113,774 B2
(45) Date of Patent: Aug. 25, 2015

(54) ELECTRONIC THERMOMETER AND BODY TEMPERATURE MEASUREMENT METHOD

(75) Inventor: Kenji Goto, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 383 days.

(21) Appl. No.: 12/973,182

(22) Filed: Dec. 20, 2010

(65) Prior Publication Data

US 2011/0158284 A1 Jun. 30, 2011

(30) Foreign Application Priority Data

Dec. 24, 2009 (JP) ................................. 2009-291953

(51) Int. Cl.
| | |
|---|---|
| *G01K 3/00* | (2006.01) |
| *G01K 7/00* | (2006.01) |
| *G01K 1/00* | (2006.01) |
| *A61B 5/00* | (2006.01) |
| *A61B 5/01* | (2006.01) |
| *G01K 7/42* | (2006.01) |
| *G01K 13/00* | (2006.01) |

(52) U.S. Cl.
CPC ................. *A61B 5/0008* (2013.01); *A61B 5/01* (2013.01); *A61B 5/6833* (2013.01); *G01K 7/42* (2013.01); *G01K 13/002* (2013.01); *A61B 2560/0252* (2013.01)

(58) Field of Classification Search
CPC ............ G01K 3/00; G01K 7/00; G01K 1/00; A61B 5/01; A61B 2018/00714; A61B 5/0008; A61B 5/0531

USPC ......... 374/120, 121, 100, 163, 183, 170, 185, 374/1, 110, 166; 600/474, 549; 340/870.17; 702/99, 130–136

See application file for complete search history.

(56) References Cited

U.S. PATENT DOCUMENTS

| | | | | |
|---|---|---|---|---|
| 3,960,138 | A * | 6/1976 | Doss et al. ..................... | 600/549 |
| 4,090,504 | A * | 5/1978 | Nathan ......................... | 600/483 |
| 5,050,612 | A * | 9/1991 | Matsumura ................... | 600/483 |
| 6,077,228 | A * | 6/2000 | Schonberger ................. | 600/549 |
| 6,086,247 | A * | 7/2000 | von Hollen ................... | 374/137 |
| 6,283,629 | B1 * | 9/2001 | Kraus et al. ...................... | 374/2 |
| 6,996,490 | B2 * | 2/2006 | Canta et al. ................... | 702/130 |
| 7,059,767 | B2 * | 6/2006 | Tokita et al. .................. | 374/163 |
| 7,249,883 | B2 | 7/2007 | Kuroda et al. | |
| 8,336,609 | B2 * | 12/2012 | Schwan et al. ................ | 165/203 |
| 2005/0101843 | A1 * | 5/2005 | Quinn et al. .................. | 600/300 |

(Continued)

FOREIGN PATENT DOCUMENTS

| | | |
|---|---|---|
| JP | 63-58223 A | 3/1988 |
| JP | 2006-308538 A | 11/2006 |

(Continued)

*Primary Examiner* — Gail Kaplan Verbitsky
(74) *Attorney, Agent, or Firm* — Global IP Counselors, LLP

(57) ABSTRACT

An electronic thermometer includes first and second body surface temperature measurement portions to measure first and second values of a measurement object, first and second reference temperature measurement portions to measure values at each position having a predetermined thermal resistance relative to a measurement position of the first and second values, and having a first and second thermal resistance relative to the open air, third temperature measurement portion to measure a third value at a different position from the previous values, correction portion to correct the obtained values; and core body temperature calculation portion to calculate a value of the object using the obtained values.

9 Claims, 19 Drawing Sheets

(56) References Cited

U.S. PATENT DOCUMENTS

2007/0055171 A1* 3/2007 Fraden .................... 600/549
2008/0214949 A1* 9/2008 Stivoric et al. ............ 600/549
2012/0238901 A1* 9/2012 Augustine ................ 600/549

FOREIGN PATENT DOCUMENTS

| JP | 2008-076144 A | 4/2008 |
| JP | 2008-128781 A | 6/2008 |

* cited by examiner

ELECTRONIC THERMOMETER AND BODY TEMPERATURE MEASUREMENT METHOD

CROSS-REFERENCE TO RELATED APPLICATIONS

This application claims priority to Japanese Patent Application No. 2009-291953 filed on Dec. 24, 2009. The entire disclosure of Japanese Patent Application No. 2009-291953 is hereby incorporated herein by reference.

BACKGROUND

1. Technological Field

The present invention relates to an electronic thermometer, and to a body temperature measurement method.

2. Background Technology

In measuring human body temperature, it is necessary to keep the thermometer under the tongue, under the armpit, in the rectum, or the like until the thermometer reaches temperature equilibrium with the body temperature. These locations reflect the temperature inside the body, referred to as the core temperature, and are generally used for body temperature measurement. A method is also used wherein a heater is mounted in a continuous core thermometer worn continuously on the body surface, and the temperature achieved when the heat current from inside the body, i.e. from the core, and the heat current from the heater become equal to each other is assumed to be the core body temperature. However, the large amount of electrical power and the control that is necessary because of the mounting of the heater result in a bulky device that cannot be used continuously on an everyday basis. Accordingly, unheated core body thermometers have been devised (Patent Documents 1, 2, 3).

In Patent Document 1, the core body temperature is calculated using temperature measuring parts of two systems having two different types of thermal resistance, and consideration is given to the thermal resistance between the temperature measuring parts of the two systems during calculation. In the temperature measuring parts, a thermistor or other temperature sensor is attached to the side close to the skin and to the side exposed to the open air, with a material having a certain thermal resistance being interposed therebetween.

In Patent Documents 2 and 3, temperature measuring parts of two systems using the same thermal resistance are used, the temperature distribution of the two different systems is determined by varying the thermal resistance on the portion in which heat is radiated out into the open air, and the core body temperature is calculated. The thermal resistance between the temperature measuring part and the human body can thereby be eliminated in terms of calculation, and there is no need to know the thermal resistance beforehand. Specifically, it is possible to measure core body temperatures very precisely without any need for the thermal resistance of each person to be measured beforehand.

PRIOR ART DOCUMENTS

Patent Document 1: Japanese Laid-open Patent Application No. 63-058223
Patent Document 2: Japanese Laid-open Patent Application No. 2006-308538
Patent Document 3: Japanese Laid-open Patent Application No. 2008-076144

SUMMARY

Problems to be Solved by the Invention

In Patent Document 1, the thermal resistance of the temperature measuring part and the thermal resistance of the human body are unknown and must be measured in advance, but measuring the thermal resistance of the human body is complicated and there are individual differences. Therefore, using a typical average value or the like may produce large errors.

Consideration has been given to the thermal resistance between the temperature sensors, but no consideration has been given to the effect produced by the thermal resistance of the end surface of the thermometer. The present inventors discovered that the effect of the end surface is larger than between the temperature sensors. This presents a concern that the heat loss near the end surface will produce an error during determination of the core body temperature.

In Patent Document 2, no consideration is given to the effect produced by the end surface of the thermometer, creating concern that the effect from the heat loss at that portion will produce an error during determination of the core body temperature.

In the three above-mentioned patent documents, no consideration is given to the temperature distribution within the body underneath the thermometer. The temperature in the external peripheral part of the thermometer is made lower than that in the center part by the horizontal movement of heat within the body, creating concern that the correct core body temperature will be impossible to derive.

Portion Used to Solve the Above-Mentioned Problems

The present invention is intended to solve at least some of the abovementioned problems, and can be implemented as the following embodiments or application examples.

APPLICATION EXAMPLE 1

An electronic thermometer characterized in comprising: first body surface temperature measurement portion to measure a first body surface temperature of a measurement object; first reference temperature measurement portion to measure, as a first reference temperature, a temperature at a position having a predetermined thermal resistance value relative to a measurement position of the first body surface temperature, and having a first thermal resistance value relative to the open air; second body surface temperature measurement portion to measure a second body surface temperature at a body surface position different from the measurement position of the first body surface temperature; second reference temperature measurement portion to measure, as a second reference temperature, a temperature at a position having a predetermined thermal resistance value relative to the measurement position of the second body surface temperature, and having a second thermal resistance value different from the first thermal resistance value relative to the open air; third temperature measurement portion to measure a third temperature at a different measurement position from the first body surface temperature and the second body surface temperature; temperature correction portion to correct the first body surface temperature, the first reference temperature, the second body surface temperature, and the second reference temperature using the third temperature; and core body temperature calculation portion to calculate a core body temperature of the measurement object using the first body surface temperature, the first reference temperature, the second body surface temperature, and the second reference temperature corrected by the temperature correction portion.

It is desirable from the standpoint of the burden on the human body for a core body thermometer that can be affixed to the body and continuously used to be small in size. However, precision problems occur and size reduction is impaired because reducing the size exacerbates the above-described problem of non-ideal temperature distribution. Accordingly, the present inventors conducted an exhaustive investigation, and as a result discovered that the core body temperature can be corrected even when the size is reduced and that a small, accurate core body thermometer can be obtained.

The first body surface temperature measurement portion and the second body surface temperature measurement portion thereby measure the first body surface temperature and the second body surface temperature of the measurement object, the first reference temperature measurement portion and the second reference temperature measurement portion measure the first and second reference temperatures, and the third temperature measurement portion measures the third temperature, whereupon the temperature correction portion corrects the first body surface temperature, the first reference temperature, the second body surface temperature, and the second reference temperature from the third temperature. The core body temperature calculation portion calculates the core body temperature of the measurement object from the first body surface temperature, the first reference temperature, the second body surface temperature, and the second reference temperature corrected by the temperature correction portion.

The temperature distribution of the body surface beneath the thermometer is measured, and the manner in which the temperature distribution within the body varies in comparison with an ideal case is determined. The measurement results are corrected on the basis of the amount of variation, allowing the core body temperature under ideal measurement conditions to be calculated. Specifically, the correct core body temperature can be measured.

Here, the core of the measurement object is defined as the region where there are fewer temperature variations than on the body surface, and where the temperature distribution is stable, and is referred to as, for example, the "core part." Accordingly, the term "core body temperature" may, for example, mean the temperature of the core part. For the temperature state within an ecological system represented by a warm-blooded animal, the term "the temperature of the core part" refers to the temperature that does not change with variations in the heat that is radiated out to the surroundings and that has an effect on the circulatory adjustment and the external regions of the body. Theoretically, the term "the temperature of the core part" designates the average temperature of the core part.

APPLICATION EXAMPLE 2

The above-described electronic thermometer is characterized in that a heat insulating part having a shared value for the predetermined thermal resistance value is provided between a measurement position of the first body surface temperature and a measurement position of the first reference temperature, and between a measurement position of the second body surface temperature and a measurement position of the second reference temperature; a first heat radiation control part having the first thermal resistance value is provided between the measurement position of the first reference temperature and the open air; and a second heat radiation control part having the second thermal resistance value is provided between the measurement position of the second reference temperature and the open air.

The first body surface temperature measurement portion and the second body surface temperature measurement portion are thereby covered by heat insulating parts having a shared value for the thermal resistance. In this case, a heat insulating part is positioned between each of the measurement positions of the body surface temperatures and the measurement positions of the reference temperatures. First and second heat radiation control parts having thermal resistance values that differ from each other are respectively provided between the measurement positions of the reference temperatures and the open air. Accordingly, the thermal flux value between the first body surface temperature measurement position and the first reference temperature measurement position, and the thermal flux value between the second body surface temperature measurement position and the second reference temperature measurement position are different from each other. Specifically, measuring the first body surface temperature, the first reference temperature, the second body surface temperature, and the second reference temperature produces mutually different values.

In the core body temperature calculation portion, providing the heat insulating parts for covering the first and second body surface temperature measurement portion with a shared value for the thermal resistance allows the thermal resistance value to be eliminated for calculation purposes, and the core body temperature of the measurement object to be calculated using the first body surface temperature, the first reference temperature, the second body surface temperature, and the second reference temperature values.

Accordingly, the core body temperature of the measurement object can be calculated regardless of the thermal resistance value from the core to the body surface that is characteristic of the measurement object, and the core body temperature of the measurement object can therefore be accurately calculated using the plurality of temperature measurement portion provided to the heat insulating part. This is true even when there are variations in the heat-transfer characteristics due to differences in body type of the measurement objects, contact with clothes or bedding, or the like.

APPLICATION EXAMPLE 3

The above-described electronic thermometer is characterized in comprising a display device having a display part for displaying the core body temperature calculated by the core body temperature calculation portion; a thermometer assembly having the first body surface temperature measurement portion and the second body surface temperature measurement portion; and the display device and the thermometer assembly being configured as separate units.

The display device and the thermometer assembly are thus configured as separate units, facilitating weight reduction of the thermometer assembly having the first and second body surface temperature measurement portion, which must be in contact with the body surface of the measurement object. Accordingly, body temperature can be monitored over a long period of time without placing a burden on the measurement object, even when the thermometer assembly is kept in contact with the body surface of the measurement object for a long period of time.

APPLICATION EXAMPLE 4

The above-described electronic thermometer is characterized in that the core body temperature calculation portion is provided to the display device.

The core body temperature calculation portion is thus provided to the display device, allowing the structural components of the thermometer assembly to be minimized. Weight and size reduction of the thermometer assembly are accordingly facilitated, and the burden placed on the measurement object can be further reduced even during a long period of measurement when the thermometer assembly is kept in contact with the body surface of the measurement object.

APPLICATION EXAMPLE 5

The above-described electronic thermometer is characterized in that the display device and the thermometer assembly each include transceiver portion capable of mutually transmitting and receiving information by wireless communication.

The display device and the thermometer assembly are thus each provided with transceiver portion, and are configured to be capable of mutual wireless communication, allowing the display device to be disposed at a certain distance from the thermometer assembly. Since the display device is not wired to the thermometer assembly, the thermometer assembly can be completely separate from the display device. Weight reduction of the thermometer assembly is therefore further facilitated, and the handling characteristics of the thermometer assembly are improved.

APPLICATION EXAMPLE 6

The above-described electronic thermometer is characterized in being configured so as to be capable of being affixed to a body surface of the measurement object.

The thermometer is thus configured so as to be capable of being affixed to the body surface of the measurement object, dispensing with the need to hold the thermometer for a fixed amount of time as with conventional temperature measurement under the tongue or the armpit, and therefore improving the operating characteristics and portability of the thermometer. For example, it is difficult to maintain adequate contact between the thermometer and the body surface for a fixed amount of time when the thermometer is used for an infant or small child, or the like. Even in such a case, contact between the body surface and the thermometer can be effectively maintained when the infant or small child moves because the thermometer is configured to be capable of being affixed to the body surface, allowing the temperature to be measured accurately.

APPLICATION EXAMPLE 7

A body temperature measurement method for measuring a core body temperature of a measurement object, characterized in comprising a first temperature measurement step for measuring a first body surface temperature of the measurement object, and for measuring, as a first reference temperature, a temperature at a position having a predetermined thermal resistance value relative to a measurement position of the first body surface temperature, and having a first thermal resistance value relative to the open air; a second temperature measurement step for measuring a second body surface temperature at a body surface position different from the measurement position of the first body surface temperature, and for measuring, as a second reference temperature, a temperature at a position having a predetermined thermal resistance value relative to the measurement position of the second body surface temperature, and having a second thermal resistance value different from the first thermal resistance value relative to the open air; a third temperature measurement step for measuring a third temperature at a position different from the measurement positions of the first body surface temperature and the second body surface temperature; a temperature correction step for correcting the first body surface temperature, the first reference temperature, the second body surface temperature, and the second reference temperature using the third temperature; and a core body temperature calculation step for calculating the core body temperature on the basis of the first body surface temperature, the first reference temperature, the second body surface temperature, and the second reference temperature corrected in the temperature correction step.

When the third temperature is thus obtained in the third temperature measurement step, the first body surface temperature, the first reference temperature, the second body surface temperature, and the second reference temperature obtained in the first temperature measurement step and the second temperature measurement step are corrected in the temperature correction step on the basis of this measurement value. The core body temperature of the measurement object is then calculated in the core body temperature calculation step on the basis of the measurement values corrected in the measurement correction step.

The core body temperature under ideal measurement conditions can be calculated by measuring the temperature distribution of the body surface underneath the thermometer, determining the manner in which the temperature distribution within the body varies in comparison with an ideal case, and correcting the measurement results on the basis of that amount of variance. Specifically, the correct core body temperature can be measured.

DETAILED DESCRIPTION OF EXEMPLARY EMBODIMENTS

The present embodiments will be described below based on the accompanying drawings.

Figure 1:
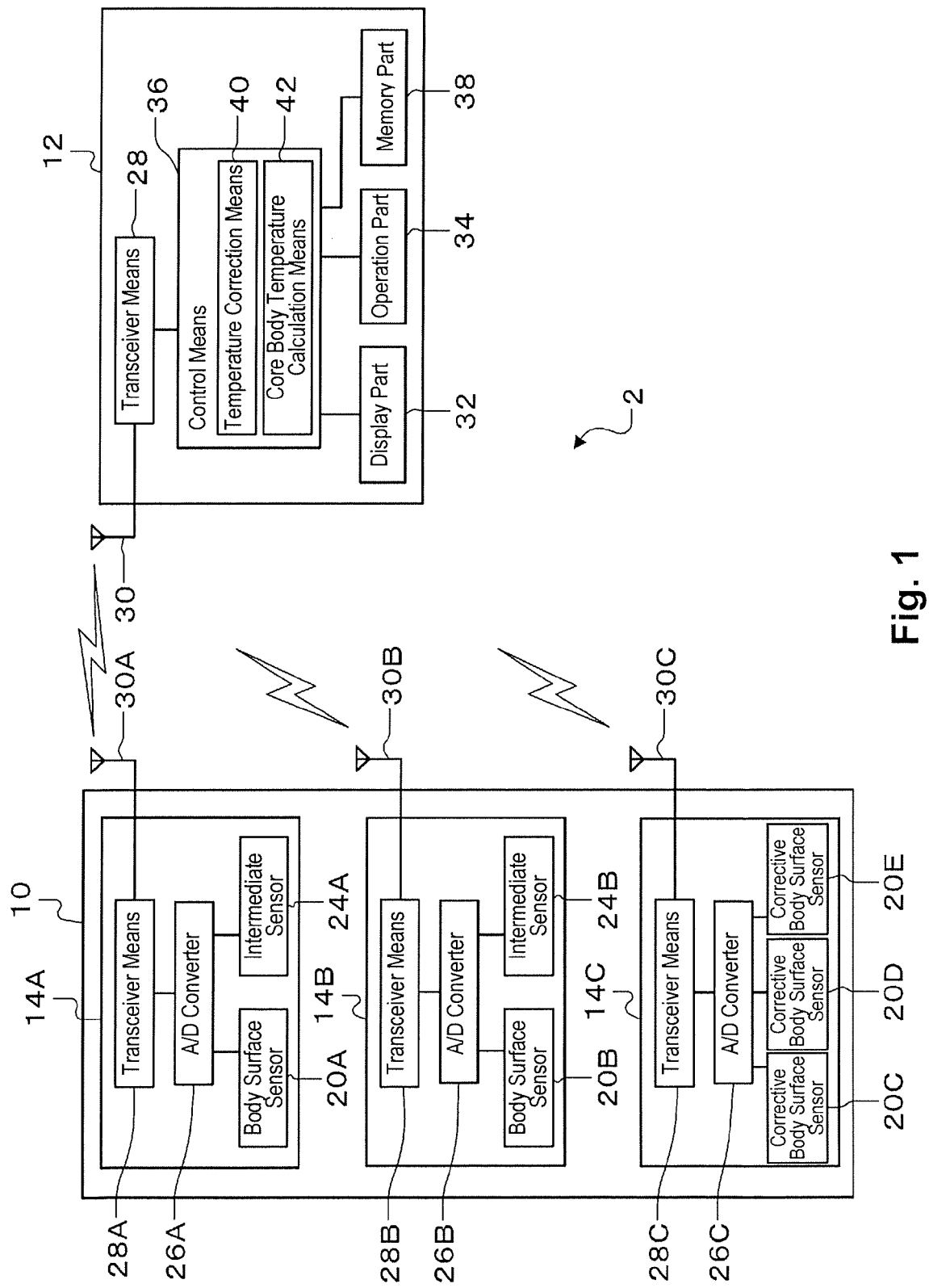
FIG. 1 is a block diagram showing an electronic thermometer according to the present embodiment.

FIG. 1 is a block configuration diagram showing an electronic thermometer according to the present embodiments. The electronic thermometer 2 has a thermometer assembly 10 in contact with the body surface 4A (see FIG. 3) of a human body 4 (see FIG. 3) as a measurement object, and a display device 12 provided separately from the thermometer assembly 10.

Figure 2:
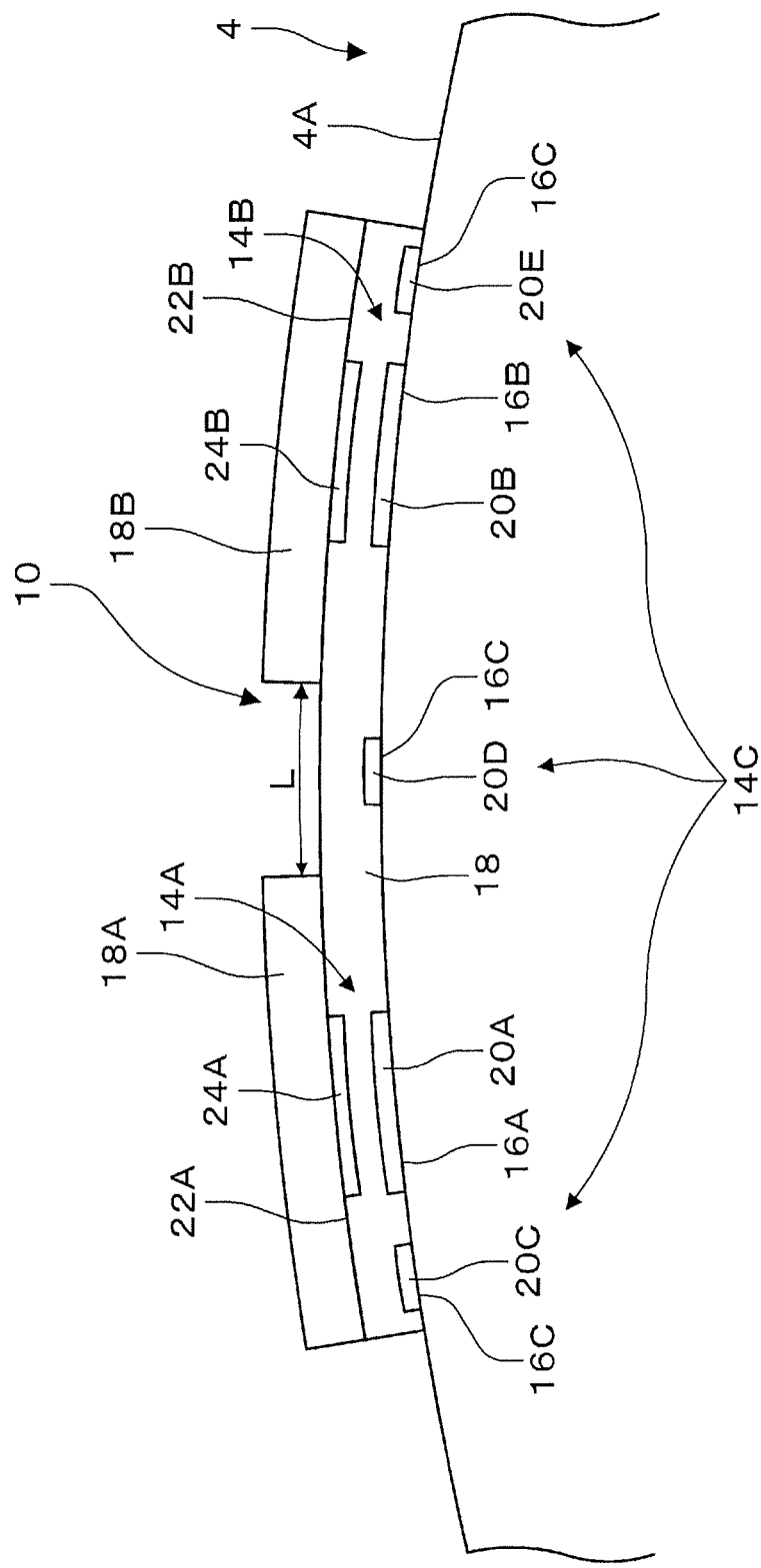
FIG. 2 is an enlarged view showing a thermometer assembly according to the present embodiment in a state of being worn on a human body.
Figure 3:
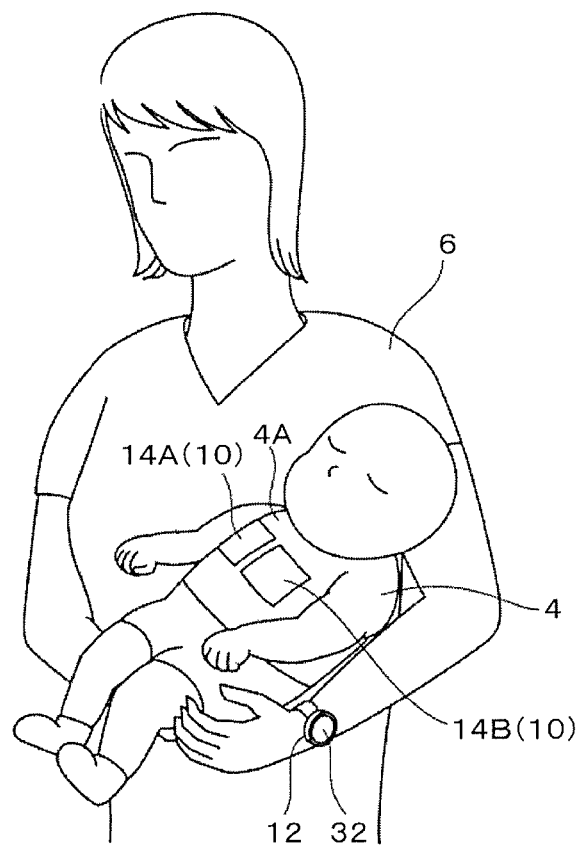
FIG. 3 is a view showing the thermometer assembly and a display device according to the present embodiment in a state of being worn.

FIG. 2 is an enlarged view showing a state in which the thermometer assembly 10 according to the present embodiment is worn on the human body 4. FIG. 3 is a view showing a state in which the thermometer assembly 10 and the display device 12 according to the present embodiment are worn on the body.

First, the thermometer assembly 10 has two (one pair of) temperature measuring parts 14A, 14B, and a temperature measuring part 14C, as shown in FIG. 2. The temperature measuring part 14A includes a heat insulating part 18 (as a substrate) having a contact surface 16A in contact with the body surface 4A of the human body 4, and a first heat radiation control part 18A provided between the heat insulating part 18 and the open air. The temperature measuring part 14B includes the heat insulating part 18 having a contact surface 16B in contact with the body surface 4A at a different position than the contact position of the temperature measuring part 14A, and a second heat radiation control part 18B between the heat insulating part 18 and the open air. The temperature measuring part 14C includes the heat insulating part 18 having a contact surface 16C in contact with the body surface 4A of the human body 4. Specifically, the heat insulating part 18 is shared by the temperature measuring parts 14A, 14B, 14C, and has a shared value for the thermal resistance.

The temperature measuring part 14A includes a body surface sensor 20A (as a first portion) as first body surface temperature measurement portion to measure the temperature of the body surface 4A as a first body surface temperature, and an intermediate sensor 24A (as a first reference portion) as first reference temperature measurement portion (intermediate temperature measurement portion) to measure the temperature of a surface boundary 22A between the heat insulating part 18 and the first heat radiation control part 18A as a first reference temperature.

The temperature measuring part 14B includes a body surface sensor 20B (as a third portion) as second body surface temperature measurement portion to measure the temperature of the body surface 4A as a second body surface temperature, and an intermediate sensor 24B (as a third reference portion) as second reference temperature measurement portion (intermediate temperature measurement portion) to measure the temperature of a surface boundary 22B between the heat insulating part 18 and the second heat radiation control part 18B as a second reference temperature.

The temperature measuring part 14C includes corrective body surface sensors 20C, 20D, 20E (as second portions) as third temperature measurement portion to measure the temperature of the body surface 4A as a third body surface temperature (third temperature).

The thermometer assembly 10 composed of the temperature measuring parts 14A, 14B, and 14C is configured so that the contact surfaces 16A, 16B, and 16C can each be bonded to the human body 4 using an adhesive or the like, and so that the assembly can be affixed with adequate contact pressure to the body surface 4A by the adhesive or the like. In the present embodiment, the thermometer assembly 10 is affixed to the chest of an infant (human body 4).

In this case, it is preferable that the bonding position of thermometer assembly 10 be set up at the forehead or back of the head, the chest, the back, or another such region where it is possible to measure the body surface temperature in a comparatively stable manner. Clothes may be worn over the thermometer assembly 10, and the thermometer assembly 10 may be in contact with bedding.

The first heat radiation control part 18A of the temperature measuring part 14A, and the second heat radiation control part 18B of the temperature measuring part 14B are configured from different materials, whereby the thermal resistance value of the first heat radiation control part 18A and the thermal resistance value of the second heat radiation control part 18B are set to different values.

The body surface sensors 20A, 20B, the corrective body surface sensors 20C, 20D, 20E, and the intermediate sensors 24A, 24B can be devices for converting the temperature of the body surface 4A and the temperature values of the surface boundaries 22A, 22B to resistance values, converting temperature values to voltage values, or the like. A chip thermistor, a flexible substrate upon which a thermistor pattern is printed, a platinum resistance thermometer sensor, or the like can be used as the device for converting the temperature values to resistance values. A thermocouple element, a pn-junction element, a diode, or the like can be used as the device for converting the temperature values to voltage values.

The temperature measuring parts 14A, 14B, 14C are provided with A/D converters 26A, 26B, 26C and transceiver portion 28A, 28B, 28C, respectively, in addition to being provided with the body surface sensors 20A, 20B, the corrective body surface sensors 20C, 20D, 20E, and the intermediate sensors 24A, 24B, as shown in FIG. 1. Integrally forming the temperature measuring parts 14A, 14B, 14C allows the A/D converters 26A, 26B, 26C to be incorporated as a shared A/D converter, and the transceiver portion 28A, 28B, 28C to be incorporated as a shared transceiver portion.

The A/D converters 26A, 26B, 26C convert the analog signals of the resistance values or voltage values converted by the body surface sensors 20A, 20B, the corrective body surface sensors 20C, 20D, 20E, and the intermediate sensors 24A, 24B to digital signals, and output the signals to the transceiver portion 28A, 28B, 28C.

The transceiver portion 28A, 28B, 28C include antenna coils 30A, 30B, 30C, respectively, and transmit, as an electromagnetic wave, the signal of the temperature value (resistance value or voltage value) that has been converted to a digital signal by the A/D converters 26A, 26B, 26C to a display device 12. The antenna coils 30A, 30B, 30C can also be fashioned into one shared antenna coil.

The display device 12 is configured in a wristwatch-style to be portable, and is capable of being worn by an operator 6 holding the infant wearing the thermometer assembly 10, as shown in FIG. 3. The display device 12 includes transceiver portion 28 for transmitting and receiving signals to and from the thermometer assembly 10, a display part 32 for displaying body temperature measurement results and the like, an operation part 34 for operating the display device 12 from the outside, control portion 36 for controlling the operation of the display device 12, and a memory part 38 for accumulating information obtained from the transceiver portion 28, the control portion 36, and the like, as shown in FIG. 1.

The transceiver portion 28 includes an antenna coil 30, and transmits and receives electromagnetic waves to and from the antenna coils 30A, 30B, 30C of the thermometer assembly 10. The antenna coil 30 transmits electromagnetic waves to the antenna coils 30A, 30B, 30C, whereby the antenna coils 30A, 30B, 30C are caused to generate electromotive force by electromagnetic induction, and the temperature measuring parts 14A, 14B, 14C are charged. The thermometer assembly 10 is therefore driven by this electromotive force, dispensing with the need for an internal battery or other power source.

The display part 32 displays temperature information and an operation screen on a liquid crystal screen or the like, and can display, for example, a measured body surface temperature, a calculated core body temperature, and the like. In the present embodiment, the display part 32 is provided to the portion corresponding to the regular dial of a wristwatch, and the display part 32 is visible while the display device 12 is worn by the operator 6 on the wrist.

The operation part 34 is configured so as to allow information to be input to the display device 12 from a distance using a button, a lever, a key, or the like, and is configured so as to allow, for example, a menu to be selected on the screen displayed on the display part 32, or to otherwise allow the name, age, date and time of measuring the body temperature, and other information regarding the measurement object (the infant in the present embodiment) to be input.

The control portion 36 includes temperature correction portion 40 for correcting a first body surface temperature Tb1 and a second body surface temperature Tb3 from the body surface sensors 20A, 20B, as well as a first intermediate temperature Tb2 and a second intermediate temperature Tb4 from the intermediate sensors 24A, 24B, on the basis of third body surface temperatures Tb5, Tb6, Tb7 from the corrective body surface sensors 20C, 20D, 20E; and core body temperature calculation portion 42 for calculating the core body temperature Tcore of the human body 4 on the basis of a first body surface temperature Tb1' and a second body surface temperature Tb3', as well as a first intermediate temperature Tb2' and a second intermediate temperature Tb4', corrected by the temperature correction portion 40.

The temperature correction portion 40 determines the manner in which the temperature distribution within the body varies in comparison with an ideal case using the third body surface temperatures Tb5, Tb6, Tb7 obtained by the corrective body surface sensors 20C, 20D, 20E, and corrects the body surface temperatures Tb1, Tb3 and the intermediate temperatures Tb2, Tb4 transmitted from the thermometer assembly 10 on the basis of the amount of variation.

The core body temperature calculation portion 42 calculates the core body temperature Tcore of the human body 4 using the first body surface temperature Tb1', the first intermediate temperature Tb2', the second body surface temperature Tb3', and the second intermediate temperature Tb4' corrected by the temperature correction portion 40.

Figure 4:
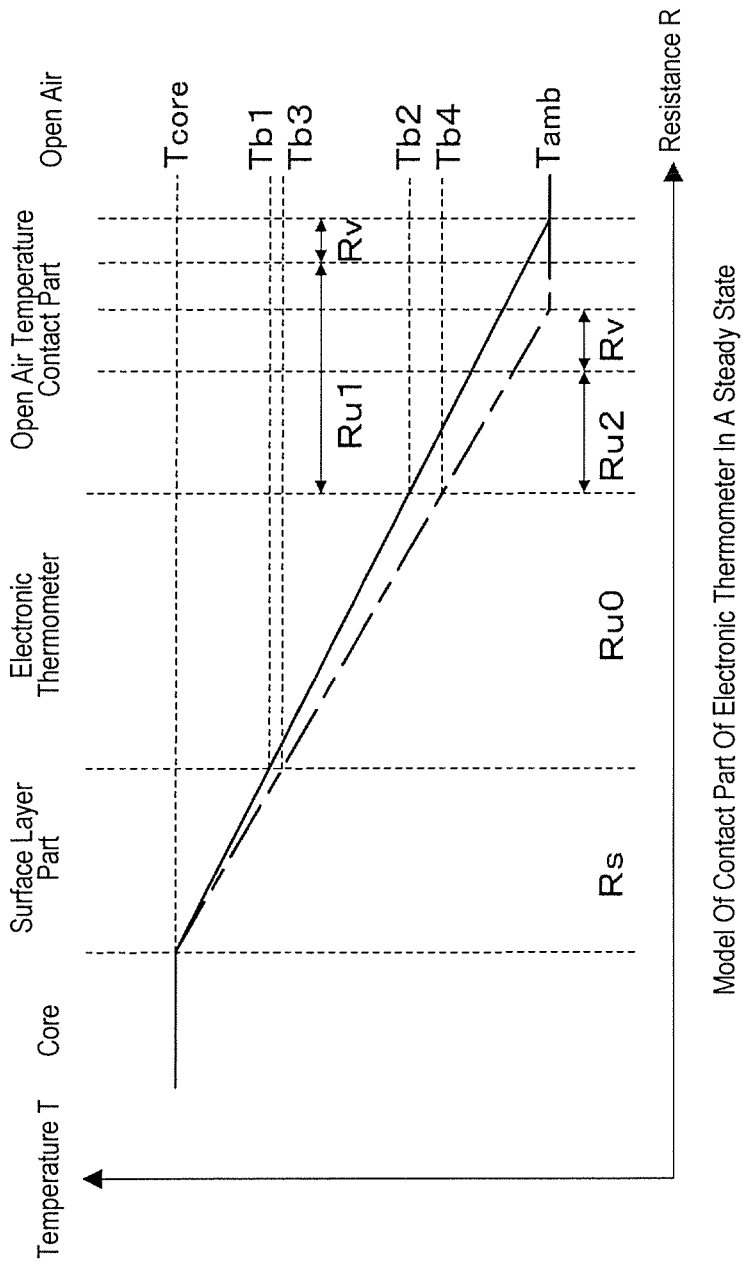
FIG. 4 is a view showing temperature distribution models of the human body and the electronic thermometer according to the present embodiment.

FIG. 4 is a view showing the temperature distribution models of the human body 4 and the electronic thermometer 2 according to the present embodiment. The drawing shows models of the temperature distribution from the core of the human body 4 through the body surface 4A and the thermometer assembly 10 to the open air. The temperature distribution models for the temperature measuring part 14A and the temperature measuring part 14B are shown by the solid line (for the temperature measuring part 14A) and the dashed line (for the temperature measuring part 14B). The vertical axis shows the temperature (T), and the horizontal axis shows the thermal resistance (R). In this case, if the relationship between the temperature (T) and the thermal resistance (R) is a straight line, the slope thereof expresses the thermal flux Q. Since the temperature distribution models for the temperature measuring part 14A and the temperature measuring part 14B display similar behavior, the description that follows will be centered on the model for the temperature measuring part 14A shown by the solid line.

In the transfer model for the temperature of the human body 4 from the core to the open air, the core body temperature Tcore of the human body 4 is substantially constant, as shown in FIG. 4. In the surface layer part closer to the outer layer than the core, the body temperature decreases due to the effects of the thermal resistance of the skin and the temperature of the open air. In actual practice, a microscopic space is formed between the body surface 4A and the contact surface 16A of the temperature measuring part 14A, and the heat release (thermal resistance value Rs) in this space therefore causes the temperature to decrease in the contact/thermal resistance part as well. Accordingly, the first body surface temperature Tb1 that has been reduced by the contact/thermal resistance part is measured in actual practice in a case where the temperature of the body surface 4A is measured by the body surface sensor 20A of the temperature measuring part 14A.

The presence of thermal resistance (thermal resistance value Ru0) in the temperature measuring part 14A itself caused by the heat insulating part 18 reduces the temperature in the temperature measuring part 14A as well, and the surface boundary 22A of the temperature measuring part 14A assumes the first intermediate temperature Tb2. The result is that the first intermediate temperature Tb2 is measured by the intermediate sensor 24A. Furthermore, the presence of the first heat radiation control part 18A having the thermal resistance value Ru1 between the open air and the surface boundary 22A of the temperature measuring part 14A causes the temperature to decrease, and the heat release (due to the thermal resistance value Rv at the contact part) at the ambient temperature contact part also causes a further decrease in temperature, leading ultimately to an ambient temperature Tamb.

In a steady state, the slope of the graph in FIG. 4 is constant because the thermal flux Q in each part is constant. At this time, if the first body surface temperature Tb1 and the first intermediate temperature Tb2 of the temperature measuring part 14A are known, the thermal flux Qu1 from the surface nearest the body surface sensor 20A of the temperature measuring part 14A to the surface boundary 22A can be calculated from the following formula (1) using the thermal resistance value Ru0.

Mathematical Formula 1

$$Qu1 = \frac{Tb1 - Tb2}{Ru0} \tag{1}$$

The thermal flux Qs+t in the portion where the surface layer part and the contact/thermal resistance part meet, i.e., the portion from the core of the human body 4 to the body surface 4A (in actual practice, the portion from the core to the contact surface 16A) is expressed by the following formula (2) using the core body temperature Tcore of the human body 4 and the thermal resistance Rs+Rt of the portion from the core of the human body 4 to the body surface 4A.

Mathematical Formula 2

$$Qs + t = \frac{Tcore - Tb1}{Rs + Rt} \tag{2}$$

In this case, the thermal resistance Rt of the contact/thermal resistance part varies with the thermal resistance value of the heat insulating part 18 of the thermometer assembly 10 in contact with the body surface 4A in addition to varying with the properties of the materials interposed in the contact/thermal resistance part. Specifically, the following formula (3), for example, may be obtained, where $\lambda 1$ is the heat transfer rate of the human body 4, $\lambda 2$ is the heat transfer rate of the thermometer assembly 10, $\delta 1$ is the surface roughness of the human body 4, $\delta 2$ is the surface roughness of the contact surface 16A of the thermometer assembly 10, P is the pressure exerted by the thermometer assembly 10 on the body surface 4A, H is the lower hardness among those of the human body 4 and the thermometer assembly 10, $\lambda f$ is the heat transfer rate of the material interposed between the body surface 4A and the contact surface 16A, $\delta f$ is the surface roughness of the interposed material, and c is a constant. The thermal resistance value Rt of the contact/thermal resistance part thus varies with a variety of conditions, and it is therefore preferable for the thermal resistance value Rt of the contact/thermal resistance part in the present embodiment to be set so as to be minimized, and to be set so that a space is not opened between the body surface 4A and the contact surface 16A. For example, applying oil to the contact portion between the body surface 4A and the contact surface 16A or other measures to improve the contact state are possible as a method for reducing the thermal resistance value Rt of the contact/thermal resistance part.

Mathematical Formula 3

$$\frac{1}{Rt} = \frac{9.70 \times 10^3}{4\sqrt{\delta 1^2 + \delta 2^2}} \cdot \frac{P}{H} \cdot \frac{\lambda 1 \lambda 2}{\lambda 1 + \lambda 2} + \frac{10^6 \lambda f}{0.25c(\delta 1 + \delta 2) + \delta f} \tag{3}$$

The thermal flux Q is constant in all the parts, and the thermal flux Qu1 within the thermometer assembly 10 and the thermal flux Qs+t in the portion from the core of the human body 4 to the body surface 4A are therefore equal to each other (Qu1=Qs+t). Accordingly, formulas (1) and (2) can be rewritten as formula (4) below, and the core body temperature Tcore can be calculated using formula (4).

Mathematical Formula 4

$$Tcore = \frac{Rs + Rt}{Ru0} \cdot (Tb1 - Tb2) + Tb1 \tag{4}$$

In this case, the thermal resistance value Rs+Rt in the portion from the core of the human body 4 to the body surface 4A is an unknown value. Accordingly, if the second body surface temperature Tb3 and the second intermediate temperature Tb4 in the temperature measuring part 14B can be obtained from the body surface sensor 20B and the intermediate sensor 24B in the same manner as with the temperature measuring part 14A, the core body temperature Tcore will be expressed as in formula (5) below.

Mathematical Formula 5

$$Tcore = \frac{Rs + Rt}{Ru0} \cdot (Tb3 - Tb4) + Tb3 \tag{5}$$

The slope of the temperature (T) in relation to the thermal resistance (R) of the temperature measuring part 14A and the temperature measuring part 14B (see FIG. 4) varies because the thermal resistance value Ru1 of the first heat radiation control part 18A and the thermal resistance value Ru2 of the second heat radiation control part 18B are set at different values. Specifically, two different relational expressions are obtained for the thermal resistance and the temperature.

When the thermal resistance value (Rs+Rt)/Ru0 is eliminated from formulas (4) and (5), the core body temperature Tcore can be calculated using formula (6) below.

Mathematical Formula 6

$$Tcore = \frac{\{Tb3 \cdot (Tb1 - Tb2) - Tb1 \cdot (Tb3 - Tb4)\}}{\{(Tb1 - Tb2) - (Tb3 - Tb4)\}} \tag{6}$$

Formula (6) is therefore stored in the core body temperature calculation portion 42 as a formula for calculating the core body temperature Tcore.

The first body surface temperature Tb1, the second body surface temperature Tb3, the first intermediate temperature Tb2, the second intermediate temperature Tb4, and the third body surface temperatures Tb5, Tb6, Tb7 transmitted from the thermometer assembly 10 are stored in the memory part 38. The first body surface temperature Tb1', the second body surface temperature Tb3', the first intermediate temperature Tb2', and the second intermediate temperature Tb4' corrected by the temperature correction portion 40 are also stored. The core body temperature Tcore of the human body 4 calculated by the core body temperature calculation portion 42 is further stored.

In this case, the memory part 38 is configured to be capable of storing temperature information relating to a plurality of human bodies 4, and stores the core body temperature Tcore and the like for each human body 4. The memory part 38 is also capable of storing the measurement position for, e.g., the first body surface temperature Tb1 and the second body surface temperature Tb3 measured when the core body temperature Tcore is to be calculated. In addition to the temperature information described above, for example, the name and age, the date the measurement was taken, and other measurement information for the measurement object (human body 4, infant) may also be stored in the memory part 38. In this case, this measurement information may be input from the operation part 34.

EXAMPLE 1

Figure 5:
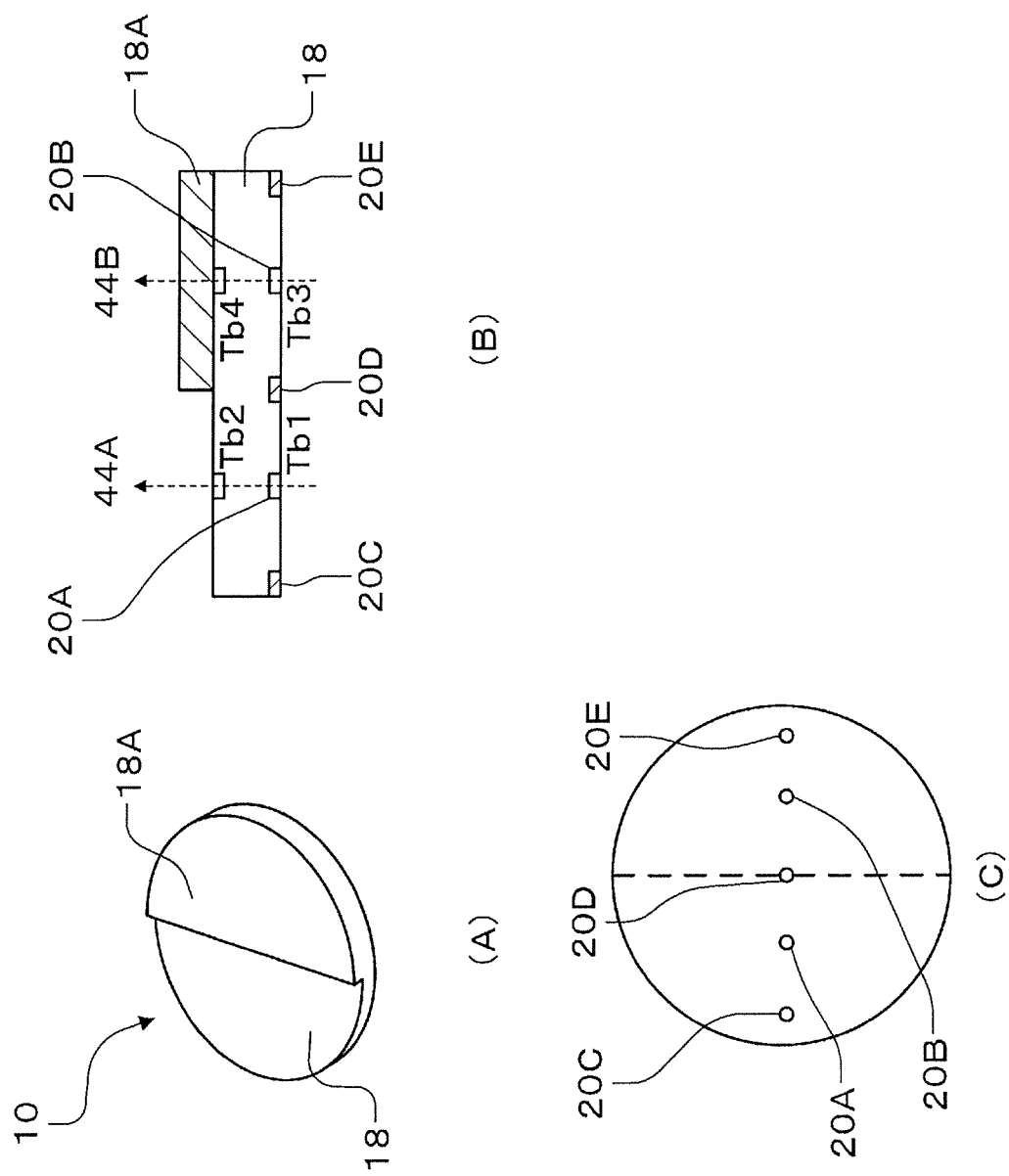
FIG. 5 is a view showing the structure of the electronic thermometer according to Example 1.

FIG. 5 is a view showing the structure of the thermometer assembly 10 according to the present example. FIG. 5(A) is a perspective view of the thermometer assembly 10, FIG. 5(B) is a cross-sectional view of the thermometer assembly 10, and FIG. 5(C) is a view showing a possible arrangement of the corrective body surface sensors 20C, 20D, 20E.

The thermometer assembly 10 has an uneven top surface and a thin, cylindrical shape, as shown in FIG. 5(A). The thermometer assembly 10 includes the body surface sensors 20A, 20B as temperature sensors (thin-film thermistors), the corrective body surface sensors 20C, 20D, 20E, and the first and second heat radiation control parts 18A, 18B, as shown in FIG. 5(B). The thermometer assembly 10 is configured so that the separate second heat radiation control part 18B having a different heat transfer rate is affixed to the top part of half of the first heat radiation control part 18A to create a temperature distribution that differs between a first system 44A and a second system 44B. In addition to the body surface sensors 20A, 20B used for measuring the core body temperature, the plurality of corrective body surface sensors 20C, 20D, 20E for measuring temperature distribution are used to obtain the temperature distribution of the skin.

The three corrective body surface sensors 20C, 20D, 20E for measuring temperature distribution are used so that one is disposed in the center of the thermometer assembly 10, and the remaining two are respectively disposed to the outside of the body surface sensors 20A, 20B used for measuring the core body temperature and located in the first and second systems 44A, 44B, as shown, for example, in FIG. 5(C).

Any material that makes it possible for the first body surface temperature Tb1 and the first intermediate temperature Tb2, as well as the second body surface temperature Tb3 and the second intermediate temperature Tb4, to differ from each other with a certain minimum precision (in this case, 0.1 degree) may be used to provide the parts with the desired heat transfer rates. For example, the heat transfer rate of the heat insulating part 18 may be about 0.2 to 0.02 W/m·K, and the heat transfer rate of the first heat radiation control part 18A may be 0.2 to 0.02 W/m·K. It is preferable, however, that the heat transfer rate of the first heat radiation control part 18A be lower than the heat transfer rate of the heat insulating part 18.

Figure 6:
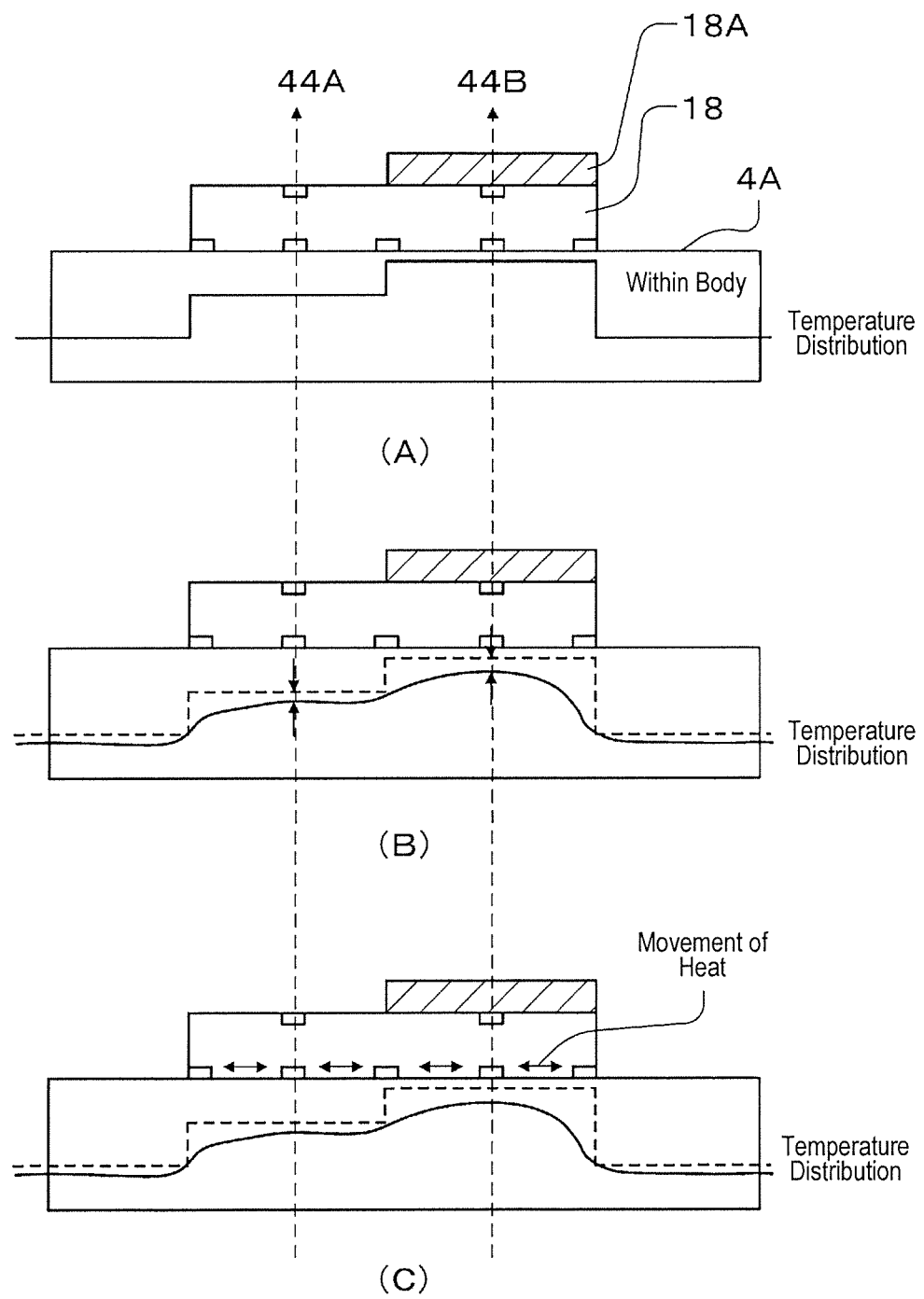
FIG. 6 is a view showing the temperature distribution of the body surface when the electronic thermometer according to Example 1 is being worn.

FIG. 6 is a view showing the temperature distribution of the body surface when the thermometer assembly 10 according to the present example is being worn. FIG. 6(A) shows the temperature distribution where there is no movement of heat in the horizontal direction, FIG. 6(B) shows the actual temperature distribution, and FIG. 6(C) shows the measurement of the movement of heat in the horizontal direction.

The temperature distribution where there is no movement of heat in the horizontal direction is a constant temperature distribution in the region on the left in the drawing where there is no heat insulating material, is an ascending distribution for the first system 44A where the first heat radiation control part 18A is located, is a distribution that rises further for the second system 44B where the first and second heat radiation control parts 18A, 18B are located, and returns to the constant temperature distribution in the region on the right in the drawing where there is no heat insulating material, as shown in FIG. 6(A).

In the actual temperature distribution, a decrease (error) in temperature due to the movement of heat in the horizontal direction occurs at points where the heat insulating material changes from being present to not being present, or vice versa, whereby the distribution is lower overall than the temperature distribution shown by the dotted line where there is no movement of heat in the horizontal direction, as shown in FIG. 6(B). Specifically, measuring the temperature distribution of the skin using the difference in temperature between the corrective body surface sensors 20C, 20D, 20E allows the movement of heat in the horizontal direction to be measured, as shown in FIG. 6(C).

Figure 7:
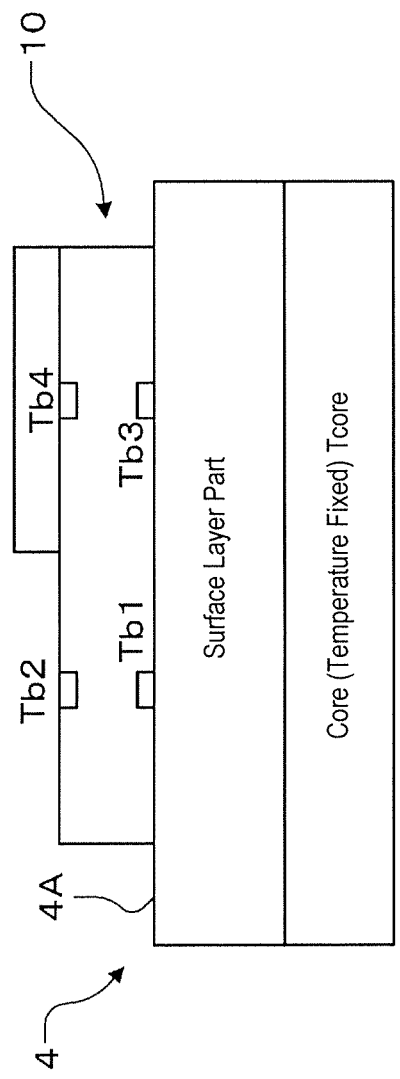
FIG. 7 is a view showing the body surface when the thermometer assembly according Example 1 is being worn.

FIG. 7 is a view showing the body surface when the thermometer assembly 10 according to the present example is being worn. In a case where the movement of heat in the horizontal direction is ignored within the surface layer part, the core body temperature Tcore can be calculated by formula (6). In an actual measurement of the core body temperature, however, the heat moves from the high-temperature part under the thermometer assembly 10 to the low-temperature part where the thermometer assembly 10 is not present, and the temperature near the end surface of the thermometer assembly 10 falls below that of the ideal state, causing an error to be generated in formula (6). This effect is particularly notable at the measurement point in a case where the thermometer assembly 10 is of a small size. A method for correcting the error is described below.

Figure 8:
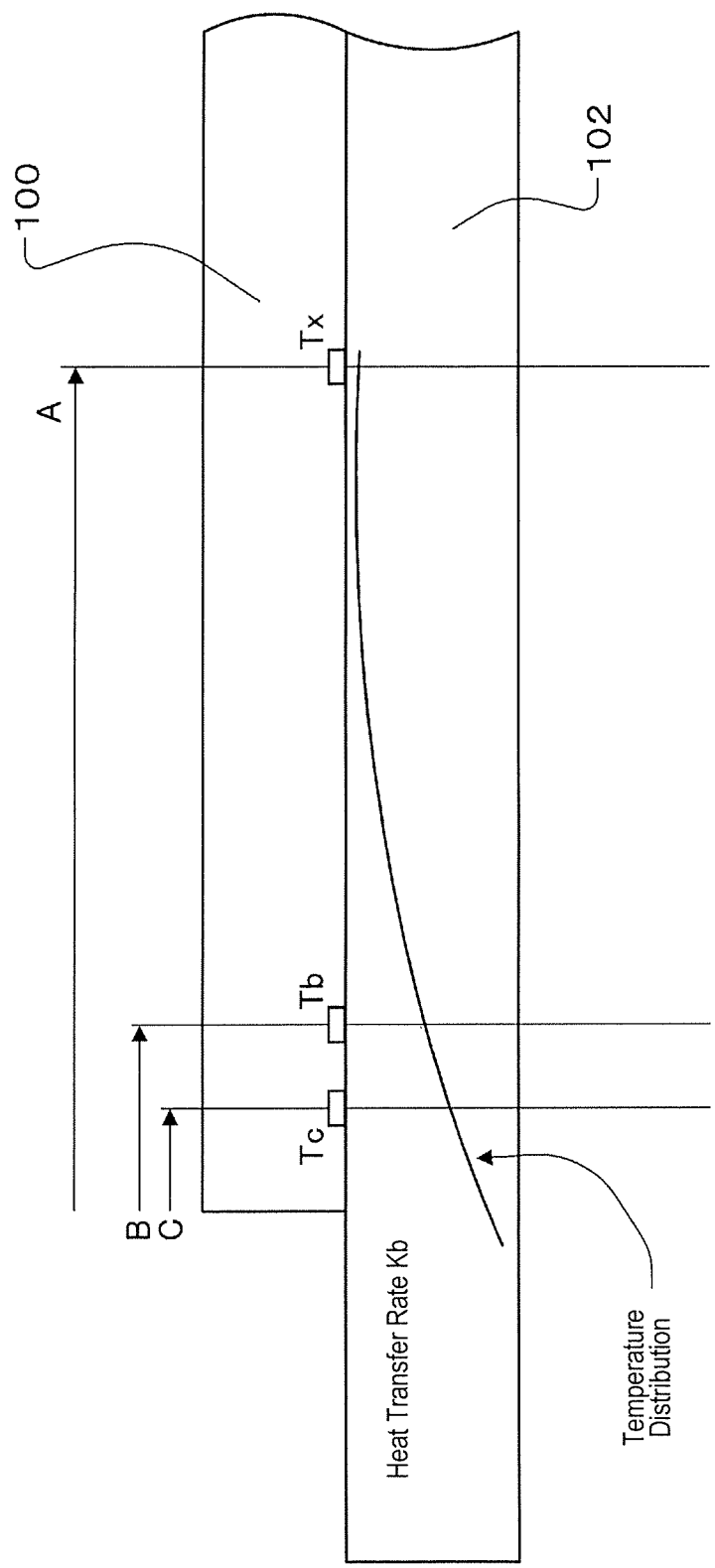
FIG. 8 is a view showing the temperature distribution of the body surface when a corrected value measuring sample according to Example 1 is being worn.

FIG. 8 is a view showing the temperature distribution of the body surface when a corrected value measuring sample according to the present example is being worn. First, in the center part, the corrected value measuring sample 100 is prepared having a size large enough to allow the effect of the end surface to be disregarded. The corrected value measuring sample 100 has the same thermal resistance as the thermometer assembly 10. A body surface layer sample 102 having a known heat transfer rate Kb is prepared, and the lower surface thereof is warmed uniformly to act as a heat source representing the core body temperature Tcore. In this case, the body surface temperature Tx at a point sufficiently far away from the end surface is regarded as the ideal value.

The temperature distribution shown in FIG. 8 is dependent on the heat transfer rate Kb of the body surface layer sample 102. Therefore, the relationship between body surface temperatures Tb and Tc and the body surface temperature Tx is measured and summarized in table form by varying the heat transfer rate Kb. This may also be obtained from a heat transfer simulation. In this case, a description has been given of a case where there are two measurement points, but the number n of measurement points may be two or more, and a greater number of measurement points produces more-accurate results for the body surface temperature Tx.

Figure 9:
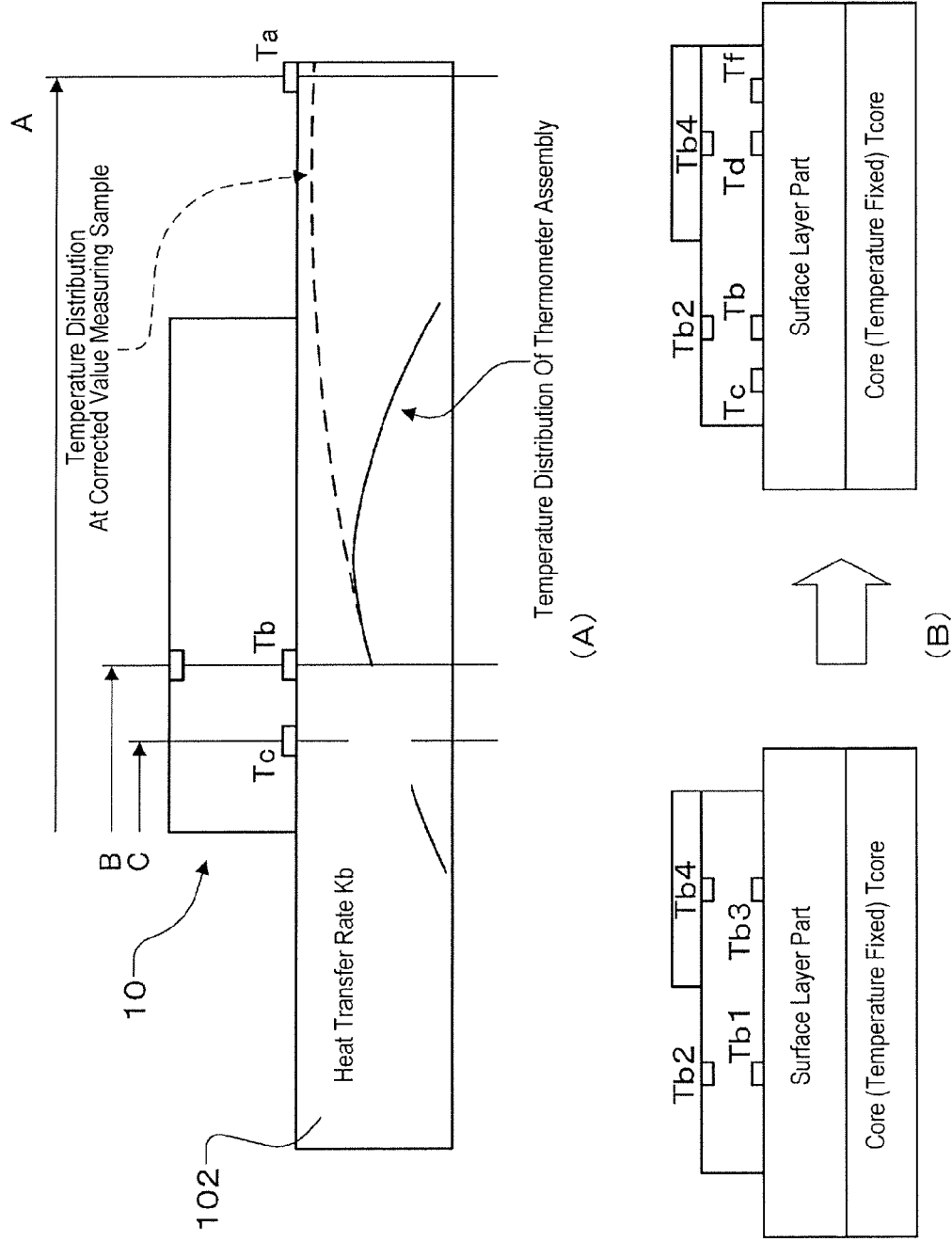
FIG. 9 is a view showing the temperature distribution of the body surface when the thermometer assembly according to Example 1 is being worn.

FIG. 9 is a view showing the temperature distribution of the body surface when the thermometer assembly 10 according to the present example is being worn. The thermometer assembly 10 of the present example should preferably be reduced in size. Therefore, the body surface temperature Tx cannot be measured directly, but the body surface temperatures Tb and Tc can be measured, allowing the body surface temperature Tx (see FIG. 8) to be estimated by calculating the body surface temperature Ta through simulation, as shown in FIG. 9(A). The same measurements or simulation can be performed for the second body surface temperature Tb3, as shown in FIG. 9(B), and an ideal value of the body surface temperature Ty (not shown) can be estimated from the body surface temperatures Td and Tf. A more accurate core body temperature Tcore can be derived by using the first body surface temperature Tx and the second body surface temperature Ty in place of the first body surface temperature Tb1 and the second body surface temperature Tb3 in the calculation formula.

Figure 10:
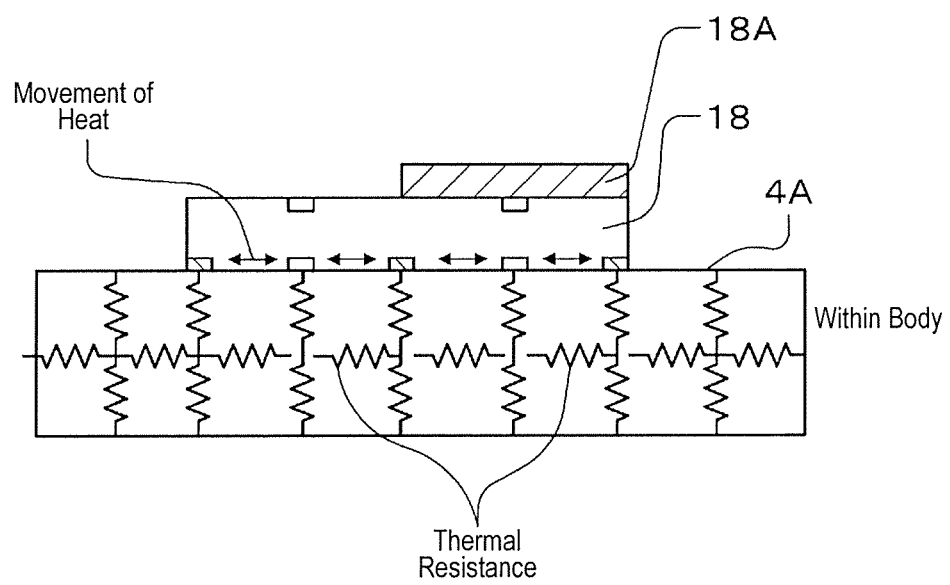
FIG. 10 is a view showing an electric equivalent circuit of a heat current in living tissue for calculating the core body temperature according to Example 1.

FIG. 10 is a view showing an electrical equivalent circuit of a heat current in living tissue for calculating the core body temperature in accordance with the present example. The movement of heat in the vertical and horizontal directions is calculated as the thermal resistance inside the body to obtain the actual temperature distribution. In the process, the temperature distribution where there is no movement of heat in the horizontal direction can be obtained by calculating the temperature distribution for a case where the thermal resistance in the horizontal direction is infinitely large. The value of each of the sensors can be corrected and the core body temperature Tcore calculated using this temperature distribution.

EXAMPLE 2

Figure 11:
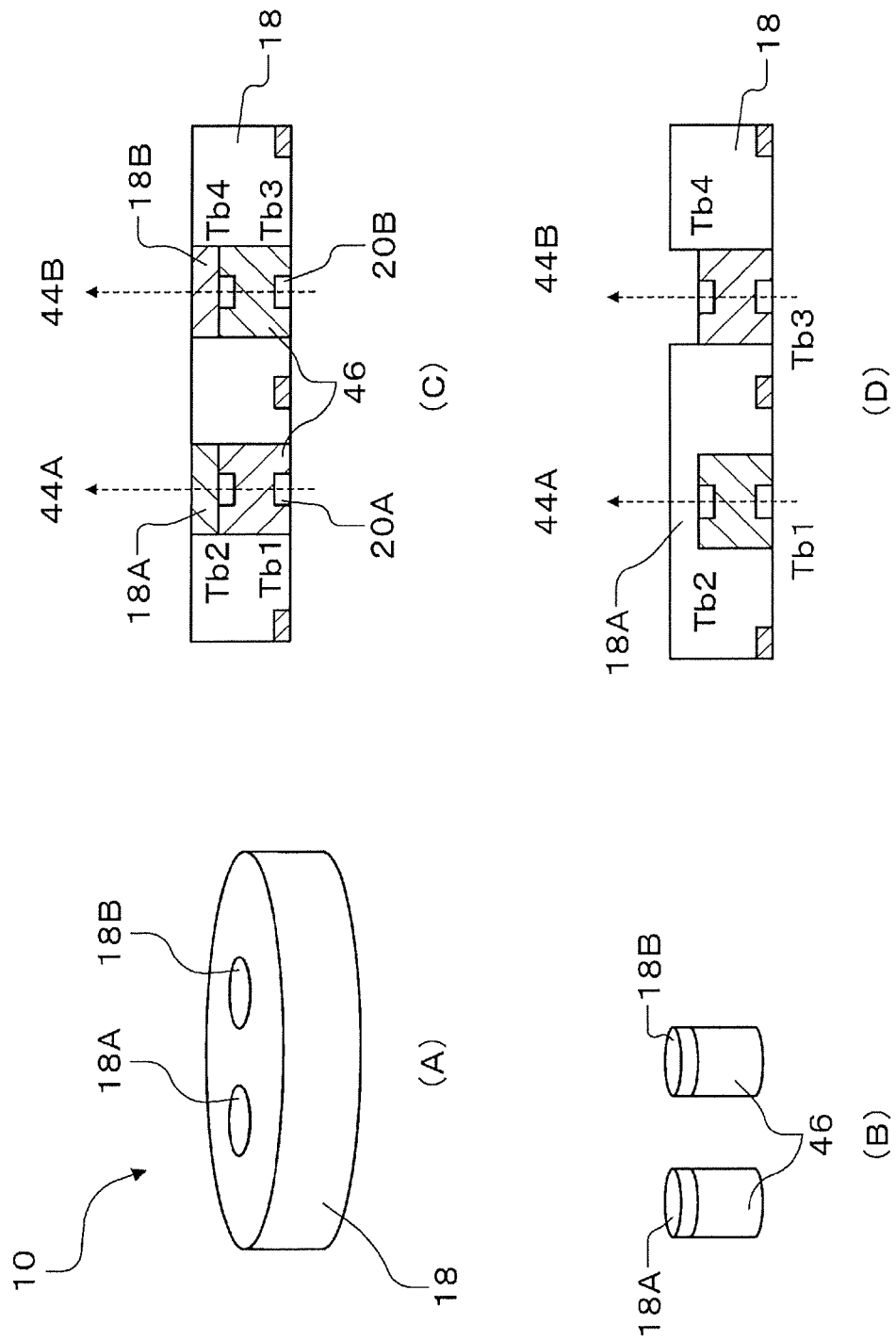
FIG. 11 is a view showing the structure of the electronic thermometer according to Example 2.

FIG. 11 is a view showing the structure of the thermometer assembly 10 according to the present example. FIG. 11(A) is a perspective view of the thermometer assembly 10, FIG. 11(B) is a cut-away view of temperature measuring parts 46, and FIGS. 11(C) and (D) are cross-sectional views of the thermometer assembly 10.

The thermometer assembly 10 is designed so that the temperature measuring parts are enclosed by the heat insulating part 18, and heat is transferred in one dimension, as shown in FIG. 11(A). The thermal resistances of the temperature measuring parts 46 in the thermometer assembly 10 are equal to each other, as shown in FIG. 11(B), but the first and second heat radiation control parts 18A, 18B provided to the assembly are composed of materials having different heat transfer rates in the portions in contact with the open air so as to obtain different temperature distributions. For example, the first and second heat radiation control parts 18A, 18B are provided to the portions in contact with the open air so that the temperature distributions in the first system 44A and the second system 44B are different from each other, as shown in FIG. 11(C). The first system 44A is provided with the first heat radiation control part 18A (heat insulating part 18), and the second system 44B is left open in the portions in contact with the open air so that the temperature distributions in the first system 44A and the second system 44B are different from each other, as shown in FIG. 11(D).

Any material that makes it possible for the first body surface temperature Tb1 and the first intermediate temperature Tb2, as well as the second body surface temperature Tb3 and the second intermediate temperature Tb4, to differ from each other with a certain minimum precision (in this case, 0.1 degree) may be used to provide the parts with the desired heat transfer rates. For example, the heat transfer rate of the temperature measuring parts 46 is about 0.2 W/m·K. The heat transfer rate of the heat insulating part 18 is about 0.04 W/m·K. The heat transfer rate of the first heat radiation control part 18A is about 0.04 W/m·K, which in this case is the same as that of the heat insulating part 18. It should be noted that the heat insulating part 18 must have a heat transfer rate that is lower than that of the temperature measuring parts 46.

In the above-described configuration, a plurality of corrective body surface sensors 20C, 20D, 20E for measuring the temperature distribution is used in addition to the body surface sensors 20A, 20B for measuring the core body temperature, and the temperature distribution of the skin is obtained.

Figure 12:
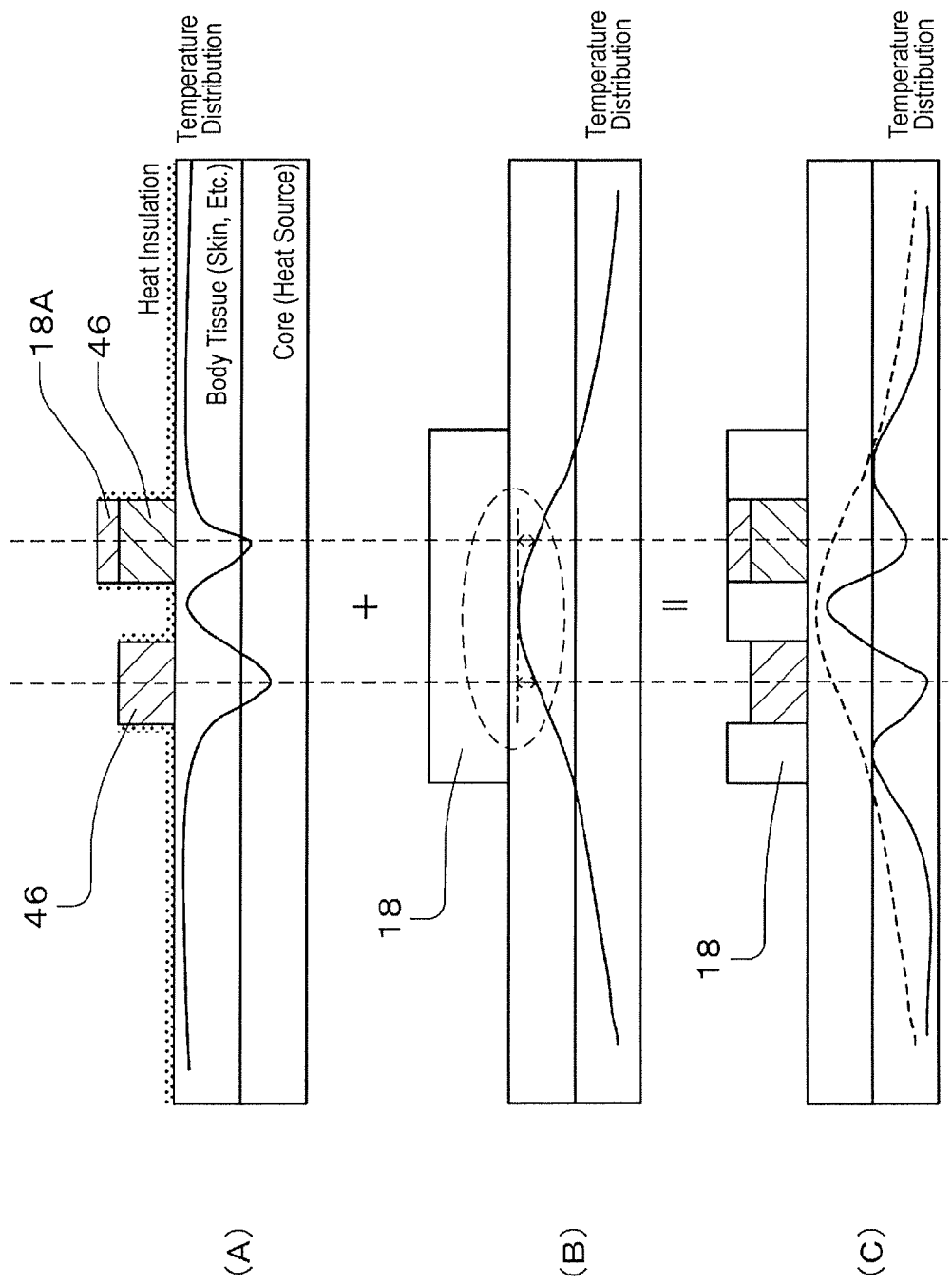
FIG. 12 is a view showing the temperature distribution of the body surface when the electronic thermometer according to Example 2 is being worn.

FIG. 12 is a view showing the temperature distribution of the body surface when the thermometer assembly 10 according to the present invention is being worn. FIG. 12(A) shows the temperature distribution when the skin surface and the side surface of the temperature measuring parts 46 are completely heat insulated, FIG. 12(B) shows the temperature distribution of the heat insulating part 18 only, and FIG. 12(C) shows the temperature distribution when the thermometer assembly 10 is being worn.

The temperature distribution when the skin surface and the side surface of the temperature measuring parts 46 are completely heat insulated is an ideal temperature distribution state because errors are minimized, as shown in FIG. 12(A).

The temperature distribution of the heat insulating part 18 alone shows heat loss appearing at the ends of the heat insulating part 18, as shown in FIG. 12(B). The heat loss at the ends of the heat insulating part 18 also affects the measurement of the temperature measuring parts 46. This effect is particularly notable when the size is reduced.

The temperature distribution when the thermometer assembly 10 is being worn is lower overall than the temperature distribution where there is no movement of heat in the horizontal direction shown by the dotted line. This is due to the fact that the temperature distribution when the skin surface and the side surface of the temperature measuring parts 46 are completely heat insulated (FIG. 12(A)) is affected by the temperature distribution of the heat insulating part 18 alone (FIG. 12(B)), and a decrease (error) in temperature is brought about by the movement of heat in the horizontal direction at the points where the heat insulating part 18 changes from being present to not being present, or vice versa, as shown in FIG. 12(C).

Figure 13:
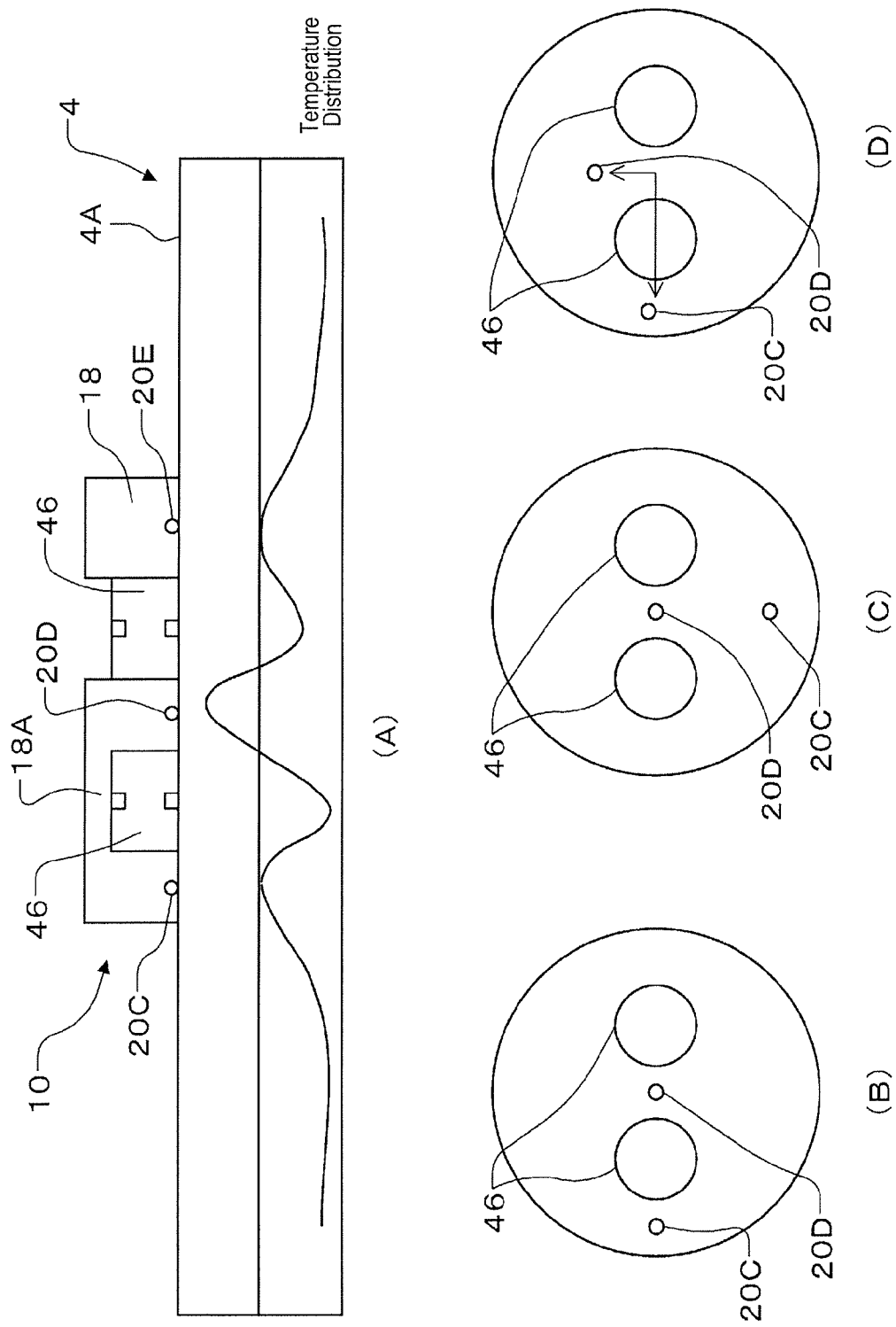
FIG. 13 is a cross-sectional view showing the temperature distribution of the body surface when the thermometer assembly according to the Example 2 is being worn, and a view showing a possible arrangement.

FIG. 13 is a cross-sectional view showing the temperature distribution of the body surface when the thermometer assembly 10 according to the present example is being worn, and a view showing a possible arrangement. FIG. 13(A) is a cross-sectional view showing the temperature distribution of the body surface when the thermometer assembly 10 is being worn, and FIGS. 13(B), (C), and (D) are views showing a possible arrangement of the corrective body surface sensors 20C, 20D. In the present example, there is a decrease in temperature because the heat transfer rate of the temperature measuring parts 46 is higher than that of the surrounding heat insulating part 18, as shown in FIG. 13. Therefore, the temperature of the temperature measuring parts 46 cannot be used directly for the corrective sensors as in Example 1. Correction portion using the corrective sensors 20C, 20D, 20E are shown herein. In this case, the corrective body surface sensors 20C, 20D may be disposed in parallel with the temperature measuring parts 46, as shown in FIG. 13(B). The corrective body surface sensors 20C, 20D may also be disposed perpendicular to the temperature measuring parts 46, as shown in FIG. 13(C). Furthermore, the corrective body surface sensors 20C, 20D may be disposed at two or more points having different distances from the center, as shown in FIG. 13(D).

Figure 14:
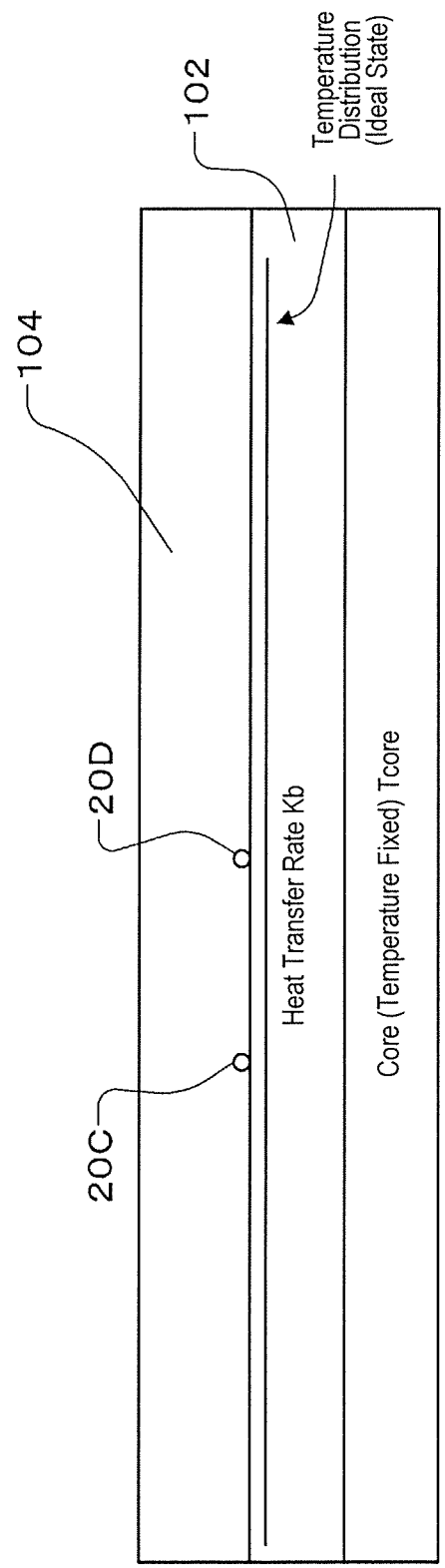
FIG. 14 is a cross-sectional view showing the temperature distribution of the body surface when the thermometer assembly according to Example 2 is being worn.
Figure 15:
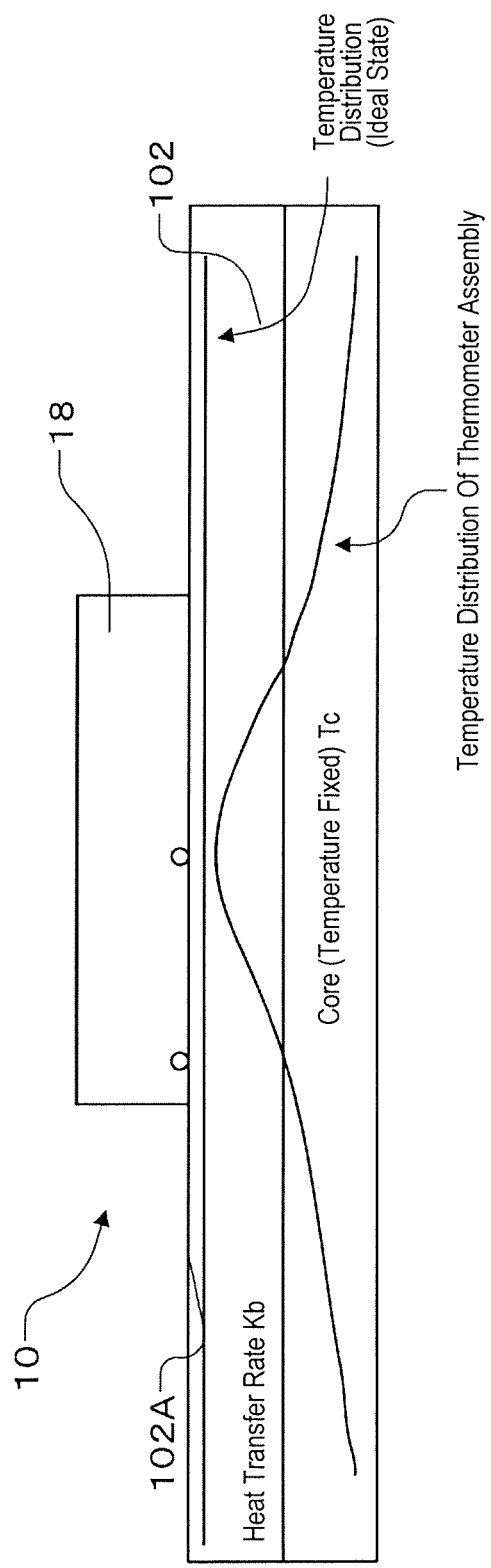
FIG. 15 is a cross-sectional view showing the temperature distribution of the body surface when the thermometer assembly according to Example 2 is being worn.

FIG. 14 is a cross-sectional view showing the temperature distribution of the body surface when the thermometer assembly 10 according to the present example is being worn. FIG. 15 is a cross-sectional view showing the temperature distribution of the body surface when the thermometer assembly 10 according to the present example is being worn. The body surface layer sample 102 having a known heat transfer rate Kb is prepared in the same manner as in Example 1, and a heat insulating material 104 of adequate size (a size sufficient to allow the heat gradient to be ignored) is placed on the top thereof. The thickness and heat transfer rate of the heat insulating material 104 are the same as for the heat insulating parts of the thermometer assembly 10. Using these, an ideal state can be measured with the corrective body surface sensors 20C, 20D.

The heat insulating part 18 of the same size in the actual thermometer assembly 10 is subsequently used to make it possible to measure the temperature distribution of the thermometer assembly 10, and the temperature distribution of the ideal state to be evaluated based on the results, as shown in FIG. 15. Since the temperature distribution of the thermometer assembly 10 is dependent on the heat transfer rate Kb of the body surface layer sample 102, the distribution is measured and summarized in a table by varying the heat transfer rate Kb to some degree.

EXAMPLE 3

Figure 16:
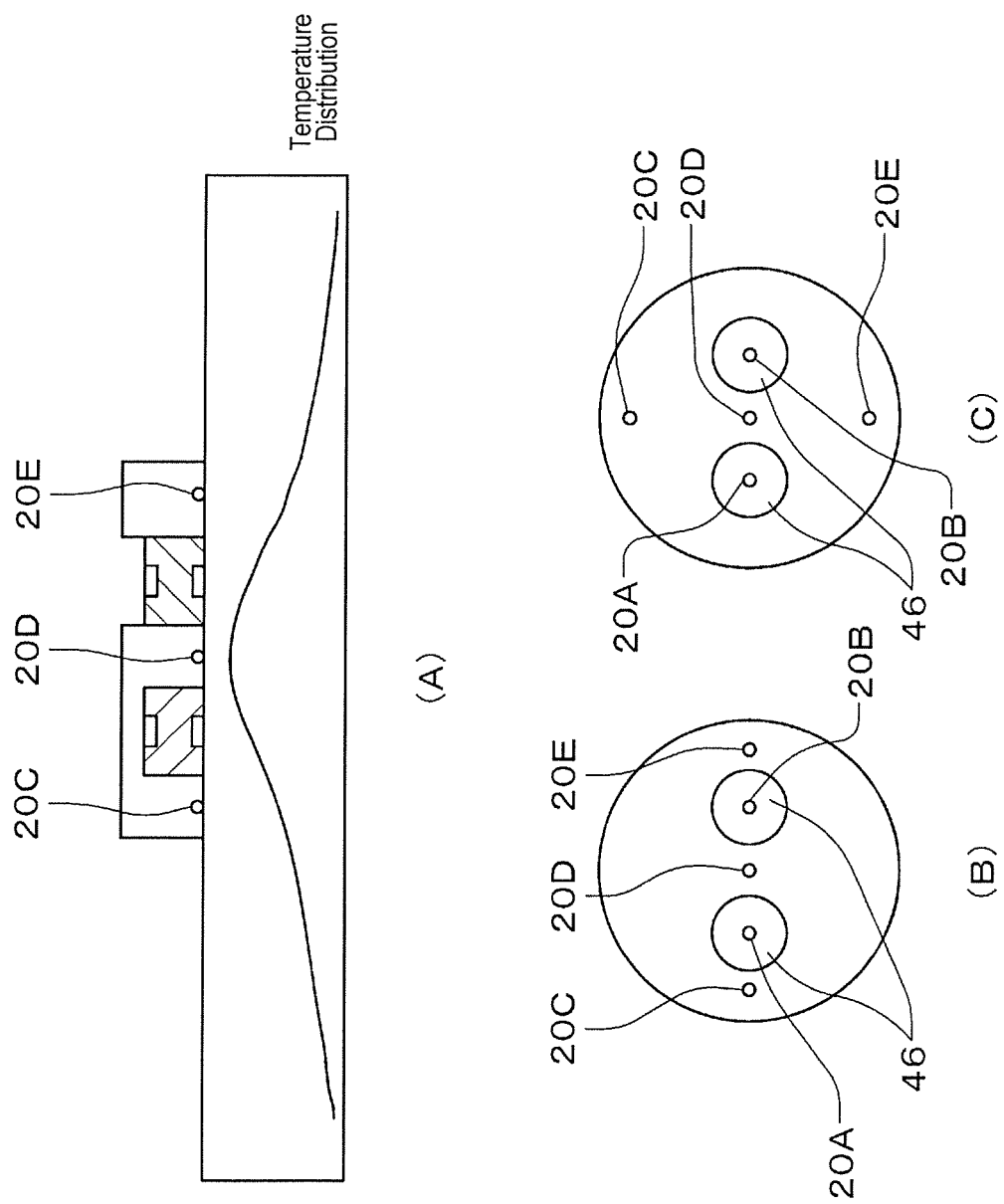
FIG. 16 is a cross-sectional view showing the temperature distribution of the body surface when the thermometer assembly according to Example 3 is being worn, and a view showing a possible arrangement.
Figure 17:
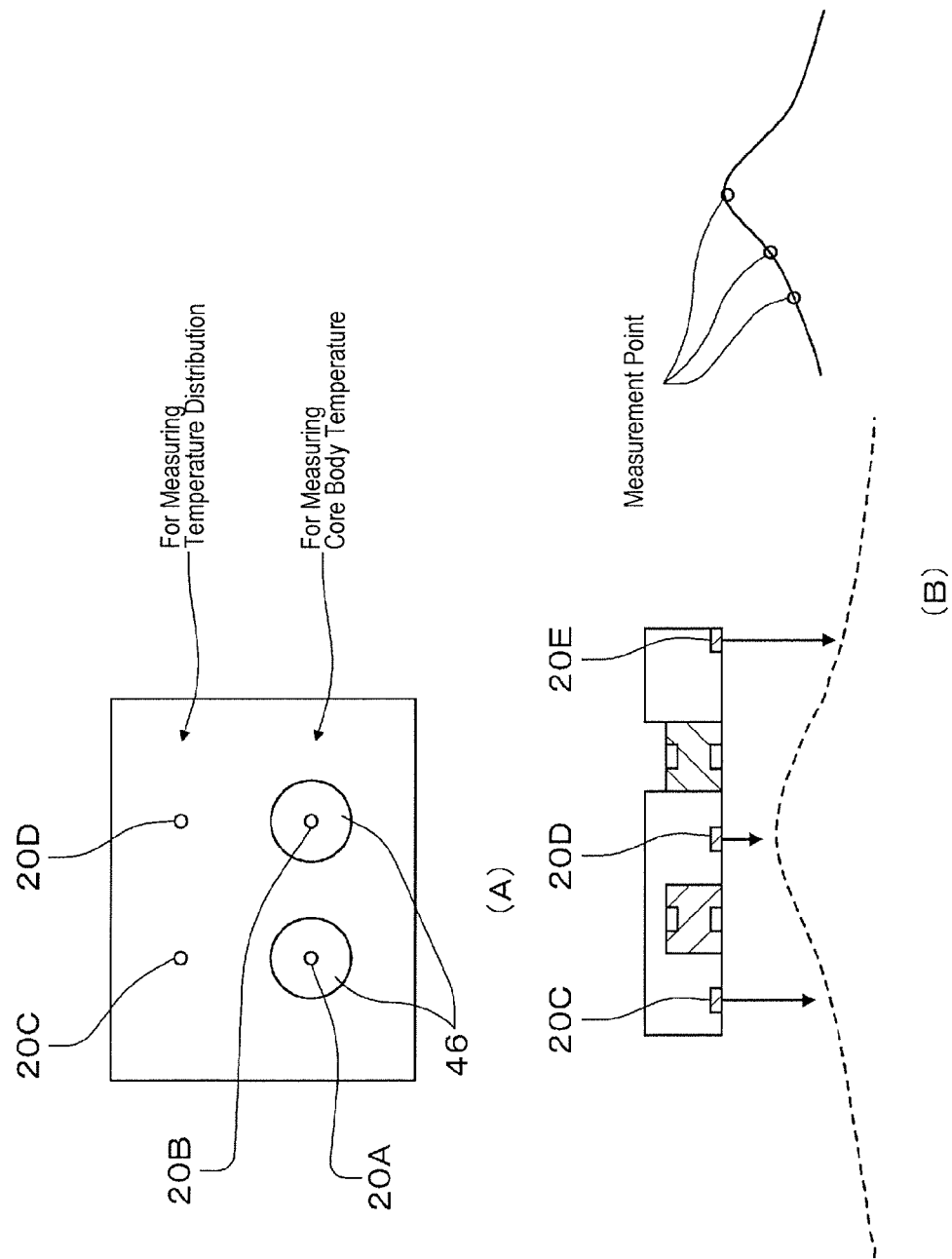
FIG. 17 is a view showing a possible arrangement of body surface sensors according to Example 3.

FIG. 16 is a cross-sectional view showing the temperature distribution of the body surface when the thermometer assembly 10 according to the present example is being worn, and a view showing a possible arrangement. FIG. 17 is a view showing a possible arrangement of the corrective body surface sensors 20C, 20D, 20E according to the present example. FIG. 16(A) is a cross-sectional view showing the temperature distribution of the body surface when the thermometer assembly 10 is being worn, and FIGS. 16(B) and (C) are views showing a possible arrangement of the corrective body surface sensors 20C, 20D, 20E.

The corrective body surface sensors 20C, 20D, 20E are added and the curve of the temperature distribution in the heat insulating part 18 alone in FIG. 12(B) is detected, as shown in FIG. 16(A). In this case, the corrective body surface sensors 20C, 20D, 20E may be disposed in parallel with the temperature measuring parts 46, as shown in FIG. 16(B). The corrective body surface sensors 20C, 20D, 20E may also be disposed perpendicular to the temperature measurement parts 46, as shown in FIG. 16(C). Furthermore, the corrective body surface sensors 20C, 20D may be disposed separately from the body surface sensors 20A, 20B for measuring the core body temperature, as shown in FIG. 17(A). This makes it possible to reduce the effect of measuring the temperature distribution and measuring the core body temperature on each other. The positions of the corrective body surface sensors 20C, 20E disposed on the exterior may be staggered to the left and right, as shown in FIG. 17(B). This produces the same state as when the gradient of the temperature distribution is measured at the three points, and allows fine gradient variations to be measured.

Figure 18:
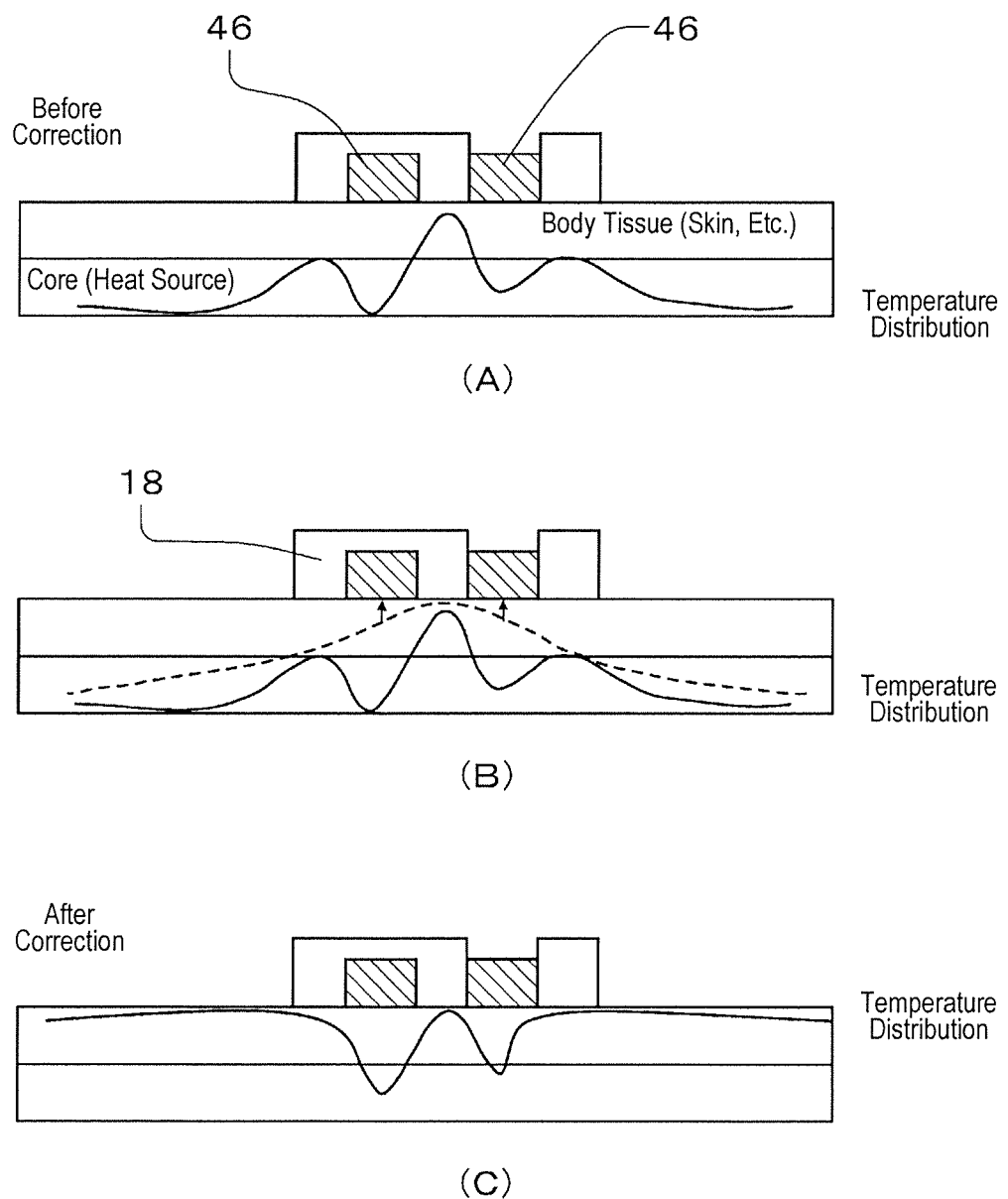
FIG. 18 is a view showing the temperature distribution of the body surface when the electronic thermometer according to Example 3 is being worn.

FIG. 18 is a view showing the temperature distribution of the body surface when the thermometer assembly 10 according to the present example is being worn. FIG. 18(A) shows the temperature distribution before correction, FIG. 18(B) shows the temperature distribution based on the corrective body surface sensors 20C, 20D, 20E for measuring the temperature distribution, and FIG. 18(C) shows the temperature distribution after correction.

As shown in FIG. 18(A), the temperature distribution before correction affects the temperature distribution based on the corrective body surface sensors 20C, 20D, 20E for measuring the temperature distribution of FIG. 18(B), and a decrease (error) in temperature is generated by the movement of heat in the horizontal direction at points where the heat insulating part 18 changes from being present to not being present, or vice versa.

The temperature distribution after correction is an ideal state of the temperature distribution because the errors are minimized, as shown in FIG. 18(C).

The electronic thermometer 2 operates in the following manner.

Figure 19:
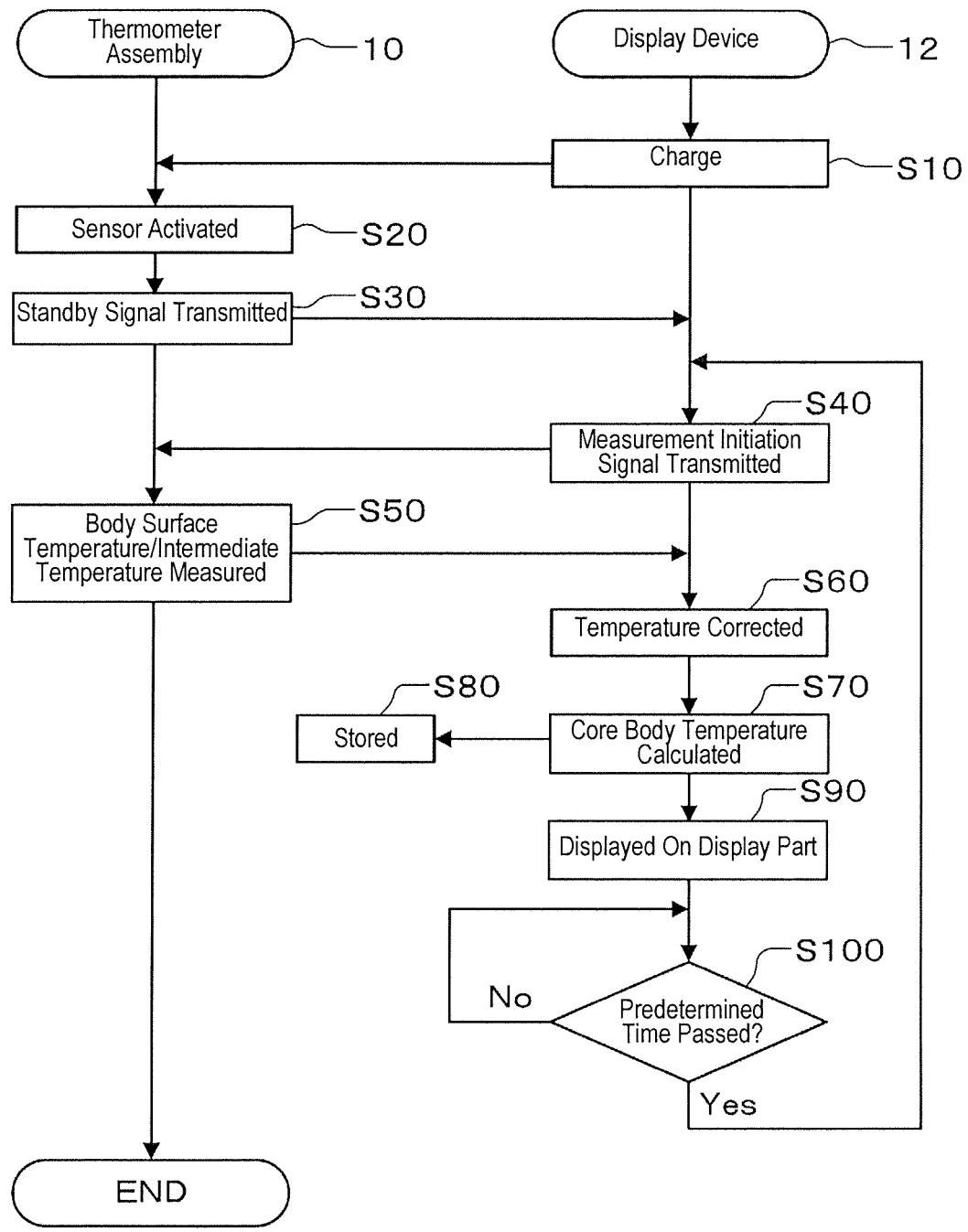
FIG. 19 is a flowchart showing the operation of the electronic thermometer according to the present embodiment.

FIG. 19 is a flowchart showing the operation of the electronic thermometer 2 according to the present embodiment.

The thermometer assembly 10 is worn on the human body 4 (on the chest of an infant in the present embodiment), and the operator 6 of the electronic thermometer 2, who is holding the infant, wears the display device 12 on the arm. When the display device 12 is switched on by the operator 6 operating the operation part 34 of the display device 12, the transceiver portion 28 transmits an electromagnetic wave to the thermometer assembly 10 (temperature measuring parts 14A, 14B, and 14C). An electromotive force is generated in the antenna coils 30A, 30B, 30C by electromagnetic induction caused by the electromagnetic wave, whereby the thermometer assembly 10 is charged (step S10).

The thermometer assembly 10 is activated by the electromotive force (step S20), as are the body surface sensors 20A, 20B, the corrective body surface sensors 20C, 20D, 2E, and the intermediate sensors 24A, 24B.

When the sensors 20A, 20B, 20C, 20D, 20E, 24A, 24B are activated, the thermometer assembly 10 transmits (step S30) a standby signal to the display device 12 from the transceiver portion 28A, 28B, 28C.

The control portion 36 of the display device 12 transmits (step S40) a temperature measurement initiation signal from the transceiver portion 28 when the standby signal is received.

The thermometer assembly 10 receives the temperature measurement initiation signal; drives the body surface sensors 20A, 20B, the corrective body surface sensors 20C, 20D, 20E, and the intermediate sensors 24A, 24B; and measures the first body surface temperature Tb1, the second body surface temperature Tb3, and the third body surface temperatures Tb5, Tb6, Tb7 of the body surface 4A, as well as the first intermediate temperature Tb2 and the second intermediate temperature Tb4 at the surface boundaries 22A, 22B (step S50; first, second, and third temperature measuring steps). Temperature information about the body surface temperatures Tb1, Tb3, Tb5, Tb6, Tb7 and about the intermediate temperatures Tb2, Tb4 is converted from an analog signal to a digital signal by the A/D converters 26A, 26B, 26C, and is transmitted to the display device 12 by the transceiver portion 28A, 28B, 28C. The body surface temperatures Tb1, Tb3, Tb5, Tb6, Tb7, as well as the intermediate temperatures Tb2, Tb4, are preferably measured after a predetermined amount of time has passed, so that the transfer of heat from the core of the human body 4 to the body surface 4A will have reached a steady state (equilibrium state).

In the temperature correction portion 40 of the control portion 36, the manner in which the temperature distribution within the body varies in comparison with an ideal case is determined from the third body surface temperatures Tb5, Tb6, Tb7 transmitted from the thermometer assembly 10; and the body surface temperatures Tb1, Tb3 and the intermediate temperatures Tb2, Tb4 transmitted from the thermometer assembly 10 are corrected based on the amount of variation (step S60, temperature correction step).

In the core body temperature calculation portion 42 of the control portion 36, the body surface temperatures Tb1', Tb3' and the intermediate temperatures Tb2', Tb4' corrected in step S60 are substituted for Tb1, Tb2, Tb3, and Tb4 of formula (6), whereby the core body temperature Tcore is calculated (step S70, core body temperature calculation step).

The control portion 36 stores (step S80) the core body temperature Tcore in the memory part 38, and displays (step S90) the core body temperature Tcore on the display part 32.

The operator 6 can ascertain the core body temperature Tcore on the display part 32 of the wristwatch-style display device 12 while holding the infant.

The control portion 36 counts the passage of time from the time of measurement of the body surface temperatures Tb1, Tb3 using a built-in timer, and monitors whether a predetermined amount of time has elapsed (step S100). If the amount of time that has elapsed is equal to or greater than the predetermined amount of time, the process returns to step S40, the control portion 36 transmits a measurement initiation signal to the thermometer assembly 10, and the body surface temperatures Tb1, Tb3, Tb5, Tb6, Tb7 are measured once again, as are the intermediate temperatures Tb2, Tb4.

The body surface temperatures Tb1, Tb3, Tb5, Tb6, Tb7 and the intermediate temperatures Tb2, Tb4 are thus measured each time the predetermined amount of time elapses, the body surface temperatures Tb1, Tb3 and the intermediate temperatures Tb2, Tb4 are corrected, and the core body temperature Tcore is calculated and stored in the memory part 38.

Effects such as the following are obtained with such an embodiment.

(1) The first body surface temperature Tb1 and the first intermediate temperature Tb2 are obtained from the temperature measuring part 14A, and the second body surface temperature Tb3 and the second intermediate temperature Tb4 are obtained from the temperature measuring part 14B. Also, the third body surface temperatures Tb5, Tb6, Tb7 are obtained from the temperature measuring part 14C, whereby the body surface temperatures Tb1, Tb3 and the intermediate temperatures Tb2, Tb4 are corrected by the temperature correction portion 40 on the basis of the third body surface temperatures Tb5, Tb6, Tb7. The core body temperature Tcore of the human body 4 can be calculated by the core body temperature calculation portion 42 from the first body surface temperature Tb1', the first intermediate temperature Tb2', the second body surface temperature Tb3', and the second intermediate temperature Tb4' corrected by the temperature correction portion 40.

The temperature distribution of the body surface beneath the thermometer is measured, and the manner in which the temperature distribution within the body varies in comparison with an ideal case is determined. The measurement results are corrected on the basis of the amount of variation, allowing the core body temperature under ideal measurement conditions to be calculated. Specifically, the correct core body temperature can be measured.

(2) The body surface temperatures Tb1, Tb3 and the intermediate temperatures Tb2, Tb4 in two types of temperature distribution (thermal flux) can be measured by using the two temperature measuring parts 14A, 14B whose overall thermal resistance values differ from each other. It is therefore possible to calculate the core body temperature Tcore solely from the measured value of the actual temperature. It is accordingly possible to calculate the core body temperature Tcore that corresponds to the actual temperature distribution to a greater degree than in a conventional case where the thermal resistance value Rs from the core of the human body to the surface layer is assumed to be, and set as, a fixed value. A more accurate core body temperature Tcore can thereby be obtained, and the measurement accuracy of the electronic thermometer 2 can be improved.

The overall thermal resistance can be set to different values by using a shared value for the thermal resistance Ru0 between the body surface temperature measurement positions and the intermediate temperature measurement positions, and varying the thermal resistance Ru1, Ru2 between the intermediate temperature measuring position and the open air. Accordingly, the thermal resistance value Ru0 between the body surface temperature measurement positions and the intermediate temperature measurement positions is prevented from being varied merely by variation in the overall thermal resistance value, even when the side of the thermometer assembly 10 exposed to the open air is in contact with clothes or bedding. Therefore, the effect of these disturbances on the measurement is reduced.

The core body temperature calculation portion 42 calculates the core body temperature Tcore of the human body 4 by utilizing the fact that the thermal flux from the core of the human body 4 to the open air is constant, dispensing with the need for a heater or other heating portion for cancelling out the heat current as with a conventional thermometer. The configuration of the electronic thermometer 2 can therefore be simplified, making it possible to further facilitate size reduction of the electronic thermometer 2. Since conventional heating portion are unnecessary, advances can be made toward lower power consumption in the electronic thermometer 2, and the electronic thermometer 2 can also be safely affixed to the body surface 4A for a long period of time. The safety and handling characteristics of the electronic thermometer 2 can therefore be improved.

(3) The core body temperature calculation portion 42 has the abovementioned formula (6) as a mathematical expression. Therefore, when the first body surface temperature Tb1', the first intermediate temperature Tb2', the second body surface temperature Tb3', and the second intermediate temperature Tb4' are obtained after correction, these values are substituted for Tb1, Tb2, Tb3, and Tb4 of formula (6), whereby the core body temperature Tcore can be calculated. The thermal resistance value Rs+Rt of the portion from the core of the human body 4 to the body surface 4A can be eliminated for calculation purposes by measuring the body surface temperature Tb1', Tb3' and the intermediate temperatures Tb2', Tb4' at two locations. Therefore, the calculation process can be simplified and accelerated without the need for using the thermal resistance value Rs+Rt. The responsiveness of the electronic thermometer 2 can accordingly be improved.

(4) The thermometer assembly 10 is configured so as to be capable of being integrally affixed to the skin of the human body 4, therefore dispensing with the need to hold the electronic thermometer 2 for a certain period of time, as with conventional measurements of temperature under the armpit or under the tongue. The handling characteristics of the thermometer assembly 10 can accordingly be improved. Since the thermometer assembly 10 is configured so as to be capable of being affixed as a single unit, the thermometer assembly 10 has good contact with the skin even when moved to some extent in cases where, for example, the thermometer is used for infants, small children, or older children. An accurate body temperature can therefore be measured. Furthermore, the core body temperature Tcore can be calculated even when clothes or bedding are in contact with the thermometer assembly 10. Body temperature can accordingly be readily and accurately measured even in a case where a continuous monitoring of temperature variations over a long period of time is desired.

For example, in a case where a woman's basal body temperature is being measured or in other similar cases, there are many restrictions on the body temperature measuring method, such as the fact that the measurement must be performed directly upon waking in the resting state, making measuring body temperature inconvenient. When measured with the electronic thermometer 2 of the present embodiment, however, body temperature can be continuously measured while the thermometer is affixed to the body surface 4A for an extended period of time. Therefore, if the thermometer assembly 10 is worn when retiring to bed, the basal body temperature can be measured automatically while sleeping, and the measurement can be already complete upon waking. The inconvenience associated with body temperature measurements can accordingly be eliminated, forgetting measurements while at home or traveling can be prevented, and accurate basal body temperatures can be reliably measured.

The electronic thermometer 2 of the present embodiment can continuously measure the body temperature of the human body 4, and is therefore also suitable for, for example, monitoring variations in body temperature of hospital inpatients or the like.

(5) The thermometer assembly 10 and the display device 12 are configured as separate units and are configured to be capable of communicating through the transceiver portion 28, 28A, 28B, 28C. The number of components installed in the thermometer assembly 10 in contact with the human body 4 can therefore be minimized, and a small, light-weight thermometer assembly 10 can be achieved. Having the thermometer assembly 10 affixed for a long period of time is thus not a burden, and the thermometer assembly 10 can therefore be made more portable. The control portion 36 including the core body temperature calculation portion 42 is provided to the display device 12, thereby further facilitating size and weight reduction of the thermometer assembly 10.

The transceiver portion 28, 28A, 28B, 28C are configured to communicate wirelessly through the antenna coils 30, 30A, 30B, 30C. Therefore, wiring and the like do not present an obstacle, improving the handling characteristics of the electronic thermometer 2.

The display device 12 is formed in a wristwatch style, and the operator 6 can therefore place the display device on the wrist and keep the display part 32 in view. It is therefore possible to check the body temperature display while holding the infant whose body temperature is being measured, as in the present embodiment, making the electronic thermometer 2 easier to operate.

(6) Electromagnetic waves are transmitted from the antenna coil 30 of the display device 12, allowing an electromotive force to be generated in the antenna coils 30A, 30B, 30C of the thermometer assembly 10 by electromagnetic induction. This electromotive force drives the thermometer assembly 10, therefore dispensing with the need for a battery or other power source in the thermometer assembly 10, and further facilitating weight and size reduction of the thermometer assembly 10.

(7) The memory part 38 can store the core body temperature Tcore and other information for a plurality of human bodies 4, allowing the electronic thermometer 2 to be used alternately among a plurality of people and to be made more convenient to use. This makes it possible to read out previous core body temperatures Tcore of measurement objects from the memory part 38 even when the electronic thermometer 2 is used by a plurality of people, and therefore makes the thermometer suitable for monitoring body temperatures over a long period of time.

(8) The heat insulating part 18 between the body surface 4A and the surface boundaries 22A, 22B has a shared value for the thermal resistance, allowing the same heat insulating material having the same thickness to be used, and an easily producible integral structure to be employed. The distance L between the temperature measuring parts 14A and 14B can also be fixed, allowing affixing to be simplified.

In the present embodiment, an ideal value based on an actual measurement (simulation) is computed, but the ideal value may also be obtained by a method using the Bessel function in a simple cylindrical form, or another method using an analytical formula.

The transceiver portion is not limited to wireless communication using antennae, but may also perform wired communication in which, for example, wiring is provided between the thermometer assembly and the display device. Such a configuration dispenses with the need for communication by electromagnetic waves, making it possible to eliminate the effect of electromagnetic waves on the human body. Also, electrical power can be supplied to the thermometer assembly using the wires, making it possible to simplify the configuration of the electrical power supply.

In the present embodiment, the body surface sensors 20A, 20B, the corrective body surface sensors 20C, 20D, 20E, and the intermediate sensors 24A, 24B include an A/D converter for converting the analog signal of the temperature value to a digital signal. However, the present invention is not limited to this option alone, and a configuration in which an A/D converter is not provided is also possible. In this case, a component for converting the temperature value to a frequency may be employed, for example, and conversion of the resistance value to a frequency may be performed using a multivibrator circuit or oscillating circuit, a V-F converter, or the like. Alternatively, a component for converting the temperature value to a time may be used. In this case, the signal converted to a frequency may be further converted to a periodic time or a pulse width.

The core body temperature calculation portion 42 is not limited to calculation portion for storing the formula (6) as a mathematical expression and calculating the core body temperature Tcore directly from the first body surface temperature Tb1, the first intermediate temperature Tb2, the second body surface temperature Tb3, and the second intermediate temperature Tb4, as in the above-described embodiment. For example, the core body temperature calculation portion 42 may be configured so that the thermal flux Q from the core of the human body to the open air, and the thermal resistance value Rs+Rt of the portion from the core of the human body to the body surface are determined, and the core body temperature Tcore is calculated using the thermal flux Q and the thermal resistance value Rs+Rt.

The surface-layer thermal resistance value Rs+Rt inherent to the human body 4 varies only slightly, allowing the previously calculated surface-layer thermal resistance value Rs+Rt to be used in a case where the electronic thermometer 2 is being used again. The time until body temperature measurement is initiated can therefore be reduced when measurement is performed the second or subsequent times. In this case, operating the operation part 34 allows a previously calculated surface-layer thermal resistance value Rs+Rt to be read out and reused if the surface-layer thermal resistance values Rs+Rt for a plurality of human bodies 4 are stored in the memory part 38. When the body temperature measurement step is performed in this case, the operation part 34 may be used to select a measurement object in order to specify the human body 4.

The thermometer is not limited to one in which the display device and the thermometer assembly are separate units, and may be configured so that the display device and the thermometer assembly form a single unit.

When the thermometer is configured so that the display device 12 and the thermometer assembly 10 constitute separate units as in the above-described embodiment, the configuration may be such that the display device 12 manages the information of a plurality of thermometer assemblies 10. ID codes for identifying each thermometer assembly 10 may be provided in this case, and a configuration may be adopted in which the thermometer assemblies 10 can be identified and managed from the display device 12.

The information from the electronic thermometer may be sent to a terminal or the like, and information from a plurality of electronic thermometers may be managed. In this case, body temperature data and the like from each measurement object can be accumulated and managed at the terminal, allowing greater ease of operation. In such a configuration, previously calculated body temperature data and the like can be retrieved from the terminal even when the electronic thermometer being used is changed. Using the electronic thermometer can therefore be made more convenient.

The reference temperature measurement portion is not limited to a case in which the first reference temperature measurement portion and the second reference temperature measurement portion are intermediate temperature measurement portion, and may also be configured so that at least one of the two is intermediate temperature measurement portion. The reference temperature measurement portion is also not limited to intermediate temperature measurement portion for measuring an intermediate temperature, and may, for example, be open air temperature measurement portion for measuring the temperature of the open air.

The body surface temperature measurement portion and the reference temperature measurement portion are not limited to being provided in pairs, and may be provided in a plurality of three or more.

In the above-described embodiment, the electronic thermometer is configured so that the thermometer assembly 10 can be affixed using adhesive, but the present invention is not limited to this configuration alone and may, for example, be configured so that the thermometer assembly 10 is incorporated into a hat or hair band, whereby the body surface temperature measurement portion can be affixed to the forehead or back of the head when the hat or hair band is worn, allowing contact with the body surface. The thermometer assembly may also be incorporated into underclothes or the like, allowing the body surface temperature measurement portion to be in contact with the back or chest by wearing the underclothes.

In the above-described embodiment, the temperature measuring parts 14A, 14B, 14C are integrally formed by a single heat insulating part 18, but a configuration in which the heat insulating part 18 is separated in two is also possible, and the temperature measuring parts 14A, 14B, 14C may be formed separately.

The shape of the display unit is not limited to a wristwatch style, and may, for example, be a free-standing unit or a unit shaped as a pendant or the like.

What is claimed is:

1. An electronic thermometer comprising:
   a first portion configured to measure a first surface temperature of a measurement object, the first portion being disposed at an inner side of a substrate;
   second portions configured to measure second surface temperatures of the measurement object, the second portions being disposed at the inner side of the substrate, the first portion and the second portions being located such that the first portion is located between the second portions, the substrate having an outer side opposed to the inner side, the inner side facing to the measurement object, and the outer side being disposed between the inner side and air;
   a first reference portion configured to measure a temperature around the substrate as a first reference temperature, the first reference portion being disposed at the outer side of the substrate;
   a correction portion configured to correct the first surface temperature and the first reference temperature based on the second surface temperatures; and
   a calculation portion configured to calculate a core temperature of the measurement object using the first surface temperature and the first reference temperature that are corrected by the correction portion.

2. The electronic thermometer of claim 1, further comprising
   a heat radiation control part provided to the first reference portion.

3. The electronic thermometer according to claim 1, further comprising a display device configured to display the core temperature calculated by the calculation portion.

4. The electronic thermometer according to claim 3, wherein
   the calculation portion is provided to the display device.

5. The electronic thermometer according to claim 3, wherein
   the display device includes a transceiver portion capable of mutually transmitting and receiving information by wireless communication.

6. The electronic thermometer according to claim 1, characterized in being capable of being affixed to a surface of the measurement object.

7. A temperature measurement method for measuring a core temperature of a measurement object, the temperature measurement method comprising:
   measuring a first surface temperature of the measurement object by a first portion and measuring second surface temperatures of the measurement object by second portions, the first portion and the second portions being disposed at an inner side of a substrate, the first portion being located between the second portions, the substrate having an outer side opposed to the inner side, the inner side facing to the measurement object, and the outer side being disposed between the inner side and air;
   measuring a temperature around the substrate as a first reference temperature by a first reference portion, the first reference portion being disposed at the outer side of the substrate;
   correcting the first surface temperature and the first reference temperature by a correction portion, using the second surface temperatures; and
   calculating the core temperature on the basis of the first surface temperature and the first reference temperature that are corrected.

8. An electronic thermometer comprising:
   a first portion configured to measure a first surface temperature of a measurement object, the first portion being disposed at an inner side of a substrate;
   a first reference portion configured to measure a temperature around the substrate as a first reference temperature, the first reference portion being disposed at an outer side of the substrate, the outer side being opposite the inner side of the substrate, the inner side facing to the measurement object, and the outer side being disposed between the inner side and air; and
   second portions configured to measure second surface temperatures of the measurement object, the second portions being disposed at the inner side of the substrate, the second portions being located such that the first portion is located between the second portions.

9. The electronic thermometer of claim 8, further comprising a third portion configured to measure a third surface temperature of a measurement object, the third portion being disposed at the inner side of the substrate, a third reference portion configured to measure a temperature around the substrate as a third reference temperature, the third reference portion being disposed at an outer side of the substrate, and the second portions being located such that the third portion is located between the second portions.

* * * * *